United States Patent
Ulich et al.

(10) Patent No.: US 7,982,018 B2
(45) Date of Patent: Jul. 19, 2011

(54) MODIFIED CORTICOTROPIN RELEASING FACTOR PEPTIDES AND USES THEREOF

(75) Inventors: Thomas R. Ulich, Flushing, NY (US); Jean-Philippe Estradier, Montreal (CA); Karen Thibaudeau, Rosemere (CA)

(73) Assignee: Conjuchem, LLC, Culver City, CA (US)

( * ) Notice: Subject to any disclaimer, the term of this patent is extended or adjusted under 35 U.S.C. 154(b) by 0 days.

(21) Appl. No.: 11/873,291

(22) Filed: Oct. 16, 2007

(65) Prior Publication Data

US 2008/0167231 A1 Jul. 10, 2008

Related U.S. Application Data

(60) Provisional application No. 60/967,281, filed on Aug. 30, 2007, provisional application No. 60/852,443, filed on Oct. 16, 2006.

(51) Int. Cl.
*A61K 38/35* (2006.01)
*A61K 38/38* (2006.01)
*C07K 14/695* (2006.01)
*C07K 14/76* (2006.01)
*C07K 14/765* (2006.01)

(52) U.S. Cl. ....... 530/402; 530/350; 530/363; 514/15.2; 514/10.8

(58) Field of Classification Search .................. None
See application file for complete search history.

(56) References Cited

U.S. PATENT DOCUMENTS

| | | | |
|---|---|---|---|
| 3,719,667 A | 3/1973 | Gutowski | |
| 3,840,556 A | 10/1974 | Kukolja | |
| 5,493,007 A | 2/1996 | Burnier et al. | |
| 5,612,034 A | 3/1997 | Pouletty et al. | |
| 5,686,511 A | 11/1997 | Bobo | |
| 5,876,969 A | 3/1999 | Fleer et al. | |
| 5,998,367 A | 12/1999 | Gaeta et al. | |
| 6,063,761 A | 5/2000 | Jones et al. | |
| 6,342,225 B1 | 1/2002 | Jones et al. | |
| 6,818,611 B1 | 11/2004 | Altman | |
| 6,838,274 B2 * | 1/2005 | Vale et al. | 435/252.3 |
| 6,849,714 B1 * | 2/2005 | Bridon et al. | 530/335 |
| 7,307,148 B2 | 12/2007 | Bousquet-Gagnon et al. | |
| 2002/0082409 A1 | 6/2002 | Hsu | |
| 2003/0165807 A1 | 9/2003 | Isfort et al. | |
| 2004/0106589 A1 | 6/2004 | Webb et al. | |
| 2006/0099571 A1 | 5/2006 | Altman | |
| 2009/0175821 A1 | 7/2009 | Bridon et al. | |

FOREIGN PATENT DOCUMENTS

| | | |
|---|---|---|
| EP | 1234586 | 8/2002 |
| WO | 92/01476 | 2/1992 |
| WO | 95/10302 | 4/1995 |
| WO | 96/29342 | 9/1996 |
| WO | 97/00063 | 1/1997 |
| WO | 99/07404 | 2/1999 |
| WO | 99/24076 | 5/1999 |
| WO | 99/25727 | 5/1999 |
| WO | 99/25728 | 5/1999 |
| WO | 00/012346 | 3/2000 |
| WO | 00/69900 | 11/2000 |
| WO | 01/17568 | 3/2001 |
| WO | 02/34934 | 5/2002 |
| WO | WO-2005/012346 A1 | 2/2005 |
| WO | 2005/099768 | 10/2005 |
| WO | 2005/103087 | 11/2005 |
| WO | 2007/049941 | 5/2007 |
| WO | 2007/071068 | 6/2007 |

OTHER PUBLICATIONS

Asakawa et al., Gastroenterology 1999, 116:1287-1292 (1999).
Campfield, Smith et al., Science 269:546-549 (1995).
Dodsworth et al,. Biotechnol. Appl. Biochem. 24:171-176 (1996).
GenBank Database, Accession No. AC005903 (Jan. 9, 2003).
GenBank Database, Accession No. AF331517 (Mar. 6, 2001).
GenBank Database, Accession No. BE622276 (Oct. 20, 2000).
Halaas, Gajiwala et al., Science 269:543-6 (1995).
Hashimoto et al., Peptides 25:1711-1721 (2004).
Hsu and Hsueh, "Human stresscopin and stresscopin-related peptide are selective ligands fOI the type 2 corticotropin-releasing hormone receptor," Nature Medicine 7: 605-611 (May 2001).
Liaw et al., Endocrinology 137:72-74, (1996).
Lewis, K. et al, "Identificiation of urocortin III, an additional member of the corticotropinreleasing factor (CRF) family with high affinity for the CRF2 receptor," Proc. Natl. Acad. Sci. USA 98(13): 7570-7575 (Jun. 19, 2001).
Lovenberg et al., PNAS USA 92:836-840 (1995).

(Continued)

*Primary Examiner* — Marianne P Allen
(74) *Attorney, Agent, or Firm* — Morrison & Foerster LLP

(57) ABSTRACT

The present invention relates to compounds comprising modified corticotrophin releasing factor peptide and specifically urocortin and urocortin-related peptides, modified derivatives thereof, and conjugates of such modified peptides and derivatives to serum components, preferably serum proteins or peptides. The compounds and conjugates of the invention comprise a reactive group, which is covalently attached to a modified peptide or derivative, optionally through a linking group. The present invention also provides methods for the covalent attachment of a modified peptide or derivative to a serum protein or peptide to form a conjugate of the invention. The conjugates of the invention preferably exhibit a longer in vivo circulating half-life compared to the corresponding unconjugated peptides. The conjugates of the invention also retain at least some of the biological activity of the unconjugated peptides, and preferably exhibit increased biological activity compared to the unconjugated peptides. The present invention also provides methods for the treatment and prevention of a disease or disorder comprising the administration of one or more of the compounds or conjugates of the invention to a subject in need of such treatment or prevention.

14 Claims, 4 Drawing Sheets

OTHER PUBLICATIONS

Pelleymounter, Cullen et al., Science 269:540-543 (1995).
Perrin et al., PNAS USA 92:2969-2973 (1995).
Perrin et al., Endocrinology 133:3058-3061 (1993).
Reyes, T.M. et al, "Urocortin II: A member of the corticotropin-releasing factor (CRF) neuropeptide family that is selectively bound by type 2 CRF receptors," Proc. Natl' Acad. Sci. USA 98(5): 2843-2848 (Feb. 27, 2001).
Stehle et al., Anticancer Drugs 8:677-685 (1997).
Takahashi et al. Peptides 25:1723-1731 (2004).
Isfort et al., "Modifications of the Human Urocortin 2 Peptide That Improve Pharmacological Properties", Peptides, 27:1806-1813, 2006.
Jetté, L. et al. (Jul. 2005, e-published Apr. 7, 2005). "Human Growth Hormone-Releasing Factor $(hGRF)_{1-19}$ Albumin Bioconjugates Activate the GRF Receptor on the Anterior Pituitary in Rats: Identification of CJC-1295 as a Long-Lasting GRF Analog," *Endocrinology*, downloaded from <http://www.endo.endojournals.org,> last visited Feb. 5, 2009, 146(7):3052-3058.

\* cited by examiner

SEQUENCE LISTING

```
<160> NUMBER OF SEQ ID NOS: 92

<210> SEQ ID NO 1
<211> LENGTH: 40
<212> TYPE: PRT
<213> ORGANISM: Homo sapiens
<220> FEATURE:
<223> OTHER INFORMATION: C-term amidated

<400> SEQUENCE: 1

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
```

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp-linker-anchor
<220> FEATURE:
<223> OTHER INFORMATION: C-term amidated

<400> SEQUENCE: 2

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 3
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Lys-epsilon-linker-anchor
<220> FEATURE:
<223> OTHER INFORMATION: C-term amidated

<400> SEQUENCE: 3

Asp Asn Pro Ser Leu Ser Ile Asp Leu Thr Phe His Leu Leu Lys Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 4
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-linker-anchor
<220> FEATURE:
<223> OTHER INFORMATION: C-term amidated

<400> SEQUENCE: 4

Asp Asn Pro Ser Leu Ser Ile Asp Leu Thr Phe His Leu Leu Arg Thr
1               5                   10                  15

Leu Leu Glu Leu Ala Lys Thr Gln Ser Gln Arg Glu Arg Ala Glu Gln
            20                  25                  30

Asn Arg Ile Ile Phe Asp Ser Val
        35                  40

```
<210> SEQ ID NO 5
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor
<220> FEATURE:
<223> OTHER INFORMATION: C-term amidated

<400> SEQUENCE: 5

Asp Asn Pro Ser Leu Ser Ile Asp Leu Thr Phe His Leu Leu Arg Thr
1               5                   10                  15

Leu Leu Glu Leu Ala Arg Thr Gln Ser Gln Lys Glu Arg Ala Glu Gln
            20                  25                  30

Asn Arg Ile Ile Phe Asp Ser Val
        35                  40

<210> SEQ ID NO 6
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Lys-epsilon-linker-anchor
<220> FEATURE:
<223> OTHER INFORMATION: C-term amidated

<400> SEQUENCE: 6

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Lys Ala Glu Gln
            20                  25                  30

Asn Arg Ile Ile Phe Asp Ser Val
        35                  40

<210> SEQ ID NO 7
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(34)
<223> OTHER INFORMATION: Lys-epsilon-linker-anchor
<220> FEATURE:
<223> OTHER INFORMATION: C-term amidated

<400> SEQUENCE: 7

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Lys Ile Ile Phe Asp Ser Val
        35                  40

<210> SEQ ID NO 8
```

```
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 8

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val Lys
        35                  40

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile-linker-anchor
<220> FEATURE:
<223> OTHER INFORMATION: C-term amidated

<400> SEQUENCE: 9

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Lys-epsilon-linker-anchor
<220> FEATURE:
<223> OTHER INFORMATION: C-term amidated

<400> SEQUENCE: 10

Ile Val Leu Ser Leu Asp Val Pro Ile Gly Leu Leu Gln Ile Leu Leu
1               5                   10                  15

Glu Gln Ala Lys Ala Arg Ala Ala Arg Glu Gln Ala Thr Thr Asn Ala
            20                  25                  30

Arg Ile Leu Ala Arg Val
        35

<210> SEQ ID NO 11
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-linker-anchor
<220> FEATURE:
<223> OTHER INFORMATION: C-term amidated

<400> SEQUENCE: 11

Ile Val Leu Ser Leu Asp Val Pro Ile Gly Leu Leu Gln Ile Leu Leu
1               5                   10                  15

Glu Gln Ala Arg Ala Lys Ala Ala Arg Glu Gln Ala Thr Thr Asn Ala
                20                  25                  30

Arg Ile Leu Ala Arg Val
            35

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Lys-epsilon-linker-anchor
<220> FEATURE:
<223> OTHER INFORMATION: C-term amidated

<400> SEQUENCE: 12

Ile Val Leu Ser Leu Asp Val Pro Ile Gly Leu Leu Gln Ile Leu Leu
1               5                   10                  15

Glu Gln Ala Arg Ala Arg Ala Ala Lys Glu Gln Ala Thr Thr Asn Ala
                20                  25                  30

Arg Ile Leu Ala Arg Val
            35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (33)..(33)
<223> OTHER INFORMATION: Lys-epsilon-linker-anchor
<220> FEATURE:
<223> OTHER INFORMATION: C-term amidated

<400> SEQUENCE: 13

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
                20                  25                  30

Lys Ile Leu Ala Arg Val
            35

<210> SEQ ID NO 14
<211> LENGTH: 38
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (37)..(37)
<223> OTHER INFORMATION: Lys-epsilon-linker-anchor
<220> FEATURE:
<223> OTHER INFORMATION: C-term amidated

<400> SEQUENCE: 14

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Lys Val
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (39)..(39)
<223> OTHER INFORMATION: Lys-epsilon-linker-anchor
<220> FEATURE:
<223> OTHER INFORMATION: C-term amidated

<400> SEQUENCE: 15

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val Lys
        35

<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe-linker-anchor
<220> FEATURE:
<223> OTHER INFORMATION: C-term amidated

<400> SEQUENCE: 16

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Asn Ala
            20                  25                  30

His Leu Met Ala Gln Ile
        35

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Phe-linker-anchor
<220> FEATURE:
<223> OTHER INFORMATION: C-term amidated

<400> SEQUENCE: 17

Phe Thr Leu Ser Leu Asp Val Pro Thr Asn Ile Met Asn Leu Leu Phe
1               5                   10                  15

Asn Ile Ala Arg Ala Lys Asn Leu Arg Ala Gln Ala Ala Ala Asn Ala
            20                  25                  30

His Leu Met Ala Gln Ile
        35

<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe-linker-anchor
<220> FEATURE:
<223> OTHER INFORMATION: C-term amidated

<400> SEQUENCE: 18

Phe Thr Leu Ser Leu Asp Val Pro Thr Asn Ile Met Asn Leu Leu Phe
1               5                   10                  15

Asn Ile Ala Lys Ala Arg Asn Leu Arg Ala Gln Ala Ala Ala Asn Ala
            20                  25                  30

His Leu Met Ala Gln Ile
        35

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe-linker-anchor
<220> FEATURE:
<223> OTHER INFORMATION: C-term amidated

<400> SEQUENCE: 19

Phe Thr Leu Ser Leu Asp Val Pro Thr Asn Ile Met Asn Leu Leu Phe
1               5                   10                  15

Asn Ile Ala Arg Ala Arg Asn Leu Arg Ala Gln Ala Ala Ala Asn Ala
            20                  25                  30

His Leu Met Ala Gln Ile
        35

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

-continued

```
<222> LOCATION: (20)..(20)
<223> OTHER INFORMATION: Lys-epsilon-linker-anchor
<220> FEATURE:
<223> OTHER INFORMATION: C-term amidated

<400> SEQUENCE: 20

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Lys-epsilon-linker-anchor
<220> FEATURE:
<223> OTHER INFORMATION: C-term amidated

<400> SEQUENCE: 21

Phe Thr Leu Ser Leu Asp Val Pro Thr Asn Ile Met Asn Leu Leu Phe
1               5                   10                  15

Asn Ile Ala Lys Ala Arg Asn Leu Arg Ala Gln Ala Ala Ala Asn Ala
            20                  25                  30

His Leu Met Ala Gln Ile
        35

<210> SEQ ID NO 22
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-linker-anchor
<220> FEATURE:
<223> OTHER INFORMATION: C-term amidated

<400> SEQUENCE: 22

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-linker-anchor
```

```
<220> FEATURE:
<223> OTHER INFORMATION: C-term amidated

<400> SEQUENCE: 23

Phe Thr Leu Ser Leu Asp Val Pro Thr Asn Ile Met Asn Leu Leu Phe
1               5                   10                  15

Asn Ile Ala Arg Ala Lys Asn Leu Arg Ala Gln Ala Ala Ala Asn Ala
            20                  25                  30

His Leu Met Ala Gln Ile
        35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Lys-epsilon-linker-anchor
<220> FEATURE:
<223> OTHER INFORMATION: C-term amidated

<400> SEQUENCE: 24

Phe Thr Leu Ser Leu Asp Val Pro Thr Asn Ile Met Asn Leu Leu Phe
1               5                   10                  15

Asn Ile Ala Lys Ala Lys Asn Leu Lys Ala Gln Ala Ala Ala Asn Ala
            20                  25                  30

His Leu Met Ala Gln Ile
        35

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Lys-epsilon-linker-anchor
<220> FEATURE:
<223> OTHER INFORMATION: C-term amidated

<400> SEQUENCE: 25

Phe Thr Leu Ser Leu Asp Val Pro Thr Asn Ile Met Asn Leu Leu Phe
1               5                   10                  15

Asn Ile Ala Arg Ala Lys Asn Leu Lys Ala Gln Ala Ala Ala Asn Ala
            20                  25                  30

His Leu Met Ala Gln Ile
        35

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Lys-epsilon-linker-anchor
<220> FEATURE:
<223> OTHER INFORMATION: C-term amidated
```

<400> SEQUENCE: 26

Phe Thr Leu Ser Leu Asp Val Pro Thr Asn Ile Met Asn Leu Leu Phe
1               5                   10                  15

Asn Ile Ala Lys Ala Arg Asn Leu Lys Ala Gln Ala Ala Ala Asn Ala
            20                  25                  30

His Leu Met Ala Gln Ile
        35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Lys-epsilon-linker-anchor
<220> FEATURE:
<223> OTHER INFORMATION: C-term amidated

<400> SEQUENCE: 27

Phe Thr Leu Ser Leu Asp Val Pro Thr Asn Ile Met Asn Leu Leu Phe
1               5                   10                  15

Asn Ile Ala Arg Ala Arg Asn Leu Lys Ala Gln Ala Ala Ala Asn Ala
            20                  25                  30

His Leu Met Ala Gln Ile
        35

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (39)..(39)
<223> OTHER INFORMATION: Lys-epsilon-linker-anchor
<220> FEATURE:
<223> OTHER INFORMATION: C-term amidated

<400> SEQUENCE: 28

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile Lys
        35

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (39)..(39)
<223> OTHER INFORMATION: Lys-epsilon-linker-anchor
<220> FEATURE:
<223> OTHER INFORMATION: C-term amidated

<400> SEQUENCE: 29

Phe Thr Leu Ser Leu Asp Val Pro Thr Asn Ile Met Asn Leu Leu Phe
1               5                   10                  15

Asn Ile Ala Arg Ala Lys Asn Leu Arg Ala Gln Ala Ala Ala Asn Ala
            20                  25                  30

His Leu Met Ala Gln Ile Lys
            35

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (39)..(39)
<223> OTHER INFORMATION: Lys-epsilon-linker-anchor
<220> FEATURE:
<223> OTHER INFORMATION: C-term amidated

<400> SEQUENCE: 30

Phe Thr Leu Ser Leu Asp Val Pro Thr Asn Ile Met Asn Leu Leu Phe
1               5                   10                  15

Asn Ile Ala Lys Ala Arg Asn Leu Arg Ala Gln Ala Ala Ala Asn Ala
            20                  25                  30

His Leu Met Ala Gln Ile Lys
            35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (39)..(39)
<223> OTHER INFORMATION: Lys-epsilon-linker-anchor
<220> FEATURE:
<223> OTHER INFORMATION: C-term amidated

<400> SEQUENCE: 31

Phe Thr Leu Ser Leu Asp Val Pro Thr Asn Ile Met Asn Leu Leu Phe
1               5                   10                  15

Asn Ile Ala Arg Ala Arg Asn Leu Arg Ala Gln Ala Ala Ala Asn Ala
            20                  25                  30

His Leu Met Ala Gln Ile Lys
            35

<210> SEQ ID NO 32
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His-anchor-linker
<220> FEATURE:
<223> OTHER INFORMATION: C-term amidated

<400> SEQUENCE: 32

His Pro Gly Ser Arg Ile Val Leu Ser Leu Asp Val Pro Ile Gly Leu

```
                1               5                  10                 15
Leu Gln Ile Leu Leu Glu Gln Ala Arg Ala Arg Ala Arg Glu Gln
            20                 25                 30

Ala Thr Thr Asn Ala Arg Ile Leu Ala Arg Val
            35                 40

<210> SEQ ID NO 33
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys-epsilon-linker-anchor
<220> FEATURE:
<223> OTHER INFORMATION: C-term amidated

<400> SEQUENCE: 33

His Pro Gly Ser Lys Ile Val Leu Ser Leu Asp Val Pro Ile Gly Leu
1               5                   10                  15

Leu Gln Ile Leu Leu Glu Gln Ala Arg Ala Arg Ala Arg Glu Gln
            20                  25                  30

Ala Thr Thr Asn Ala Arg Ile Leu Ala Arg Val
            35                  40

<210> SEQ ID NO 34
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Lys-epsilon-linker-anchor
<220> FEATURE:
<223> OTHER INFORMATION: C-term amidated

<400> SEQUENCE: 34

His Pro Gly Ser Arg Ile Val Leu Ser Leu Asp Val Pro Ile Gly Leu
1               5                   10                  15

Leu Gln Ile Leu Leu Glu Gln Ala Lys Ala Arg Ala Arg Glu Gln
            20                  25                  30

Ala Thr Thr Asn Ala Arg Ile Leu Ala Arg Val
            35                  40

<210> SEQ ID NO 35
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor
<220> FEATURE:
<223> OTHER INFORMATION: C-term amidated

<400> SEQUENCE: 35

His Pro Gly Ser Arg Ile Val Leu Ser Leu Asp Val Pro Ile Gly Leu
1               5                   10                  15
```

Leu Gln Ile Leu Leu Glu Gln Ala Arg Ala Lys Ala Ala Arg Glu Gln
            20                  25                  30

Ala Thr Thr Asn Ala Arg Ile Leu Ala Arg Val
            35                  40

<210> SEQ ID NO 36
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (30)..(30)
<223> OTHER INFORMATION: Lys-epsilon-linker-anchor
<220> FEATURE:
<223> OTHER INFORMATION: C-term amidated

<400> SEQUENCE: 36

His Pro Gly Ser Arg Ile Val Leu Ser Leu Asp Val Pro Ile Gly Leu
1               5                   10                  15

Leu Gln Ile Leu Leu Glu Gln Ala Arg Ala Arg Ala Ala Lys Glu Gln
            20                  25                  30

Ala Thr Thr Asn Ala Arg Ile Leu Ala Arg Val
            35                  40

<210> SEQ ID NO 37
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (38)..(38)
<223> OTHER INFORMATION: Lys-epsilon-linker-anchor
<220> FEATURE:
<223> OTHER INFORMATION: C-term amidated

<400> SEQUENCE: 37

His Pro Gly Ser Arg Ile Val Leu Ser Leu Asp Val Pro Ile Gly Leu
1               5                   10                  15

Leu Gln Ile Leu Leu Glu Gln Ala Arg Ala Arg Ala Ala Arg Glu Gln
            20                  25                  30

Ala Thr Thr Asn Ala Lys Ile Leu Ala Arg Val
            35                  40

<210> SEQ ID NO 38
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (42)..(42)
<223> OTHER INFORMATION: Lys-epsilon-linker-anchor
<220> FEATURE:
<223> OTHER INFORMATION: C-term amidated

<400> SEQUENCE: 38

His Pro Gly Ser Arg Ile Val Leu Ser Leu Asp Val Pro Ile Gly Leu
1               5                   10                  15

Leu Gln Ile Leu Leu Glu Gln Ala Arg Ala Arg Ala Ala Arg Glu Gln
            20                  25                  30

```
Ala Thr Thr Asn Ala Arg Ile Leu Ala Lys Val
        35                  40

<210> SEQ ID NO 39
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (44)..(44)
<223> OTHER INFORMATION: Lys-epsilon-linker-anchor
<220> FEATURE:
<223> OTHER INFORMATION: C-term amidated

<400> SEQUENCE: 39

His Pro Gly Ser Arg Ile Val Leu Ser Leu Asp Val Pro Ile Gly Leu
1               5                   10                  15

Leu Gln Ile Leu Leu Glu Gln Ala Arg Ala Arg Ala Ala Arg Glu Gln
            20                  25                  30

Ala Thr Thr Asn Ala Arg Ile Leu Ala Arg Val Lys
        35                  40

<210> SEQ ID NO 40
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr-anchor-linker
<220> FEATURE:
<223> OTHER INFORMATION: C-term amidated

<400> SEQUENCE: 40

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 41
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr-anchor-linker
<220> FEATURE:
<223> OTHER INFORMATION: C-term amidated

<400> SEQUENCE: 41

Thr Arg Phe Thr Leu Ser Leu Asp Val Pro Thr Asn Ile Met Asn Leu
1               5                   10                  15

Leu Phe Asn Ile Ala Arg Ala Arg Asn Leu Arg Ala Gln Ala Ala Ala
            20                  25                  30

Asn Ala His Leu Met Ala Gln Ile
```

35                    40

<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr-anchor-linker
<220> FEATURE:
<223> OTHER INFORMATION: C-term amidated

<400> SEQUENCE: 42

Thr Arg Phe Thr Leu Ser Leu Asp Val Pro Thr Asn Ile Met Asn Leu
1               5                   10                  15

Leu Phe Asn Ile Ala Arg Ala Lys Asn Leu Arg Ala Gln Ala Ala Ala
            20                  25                  30

Asn Ala His Leu Met Ala Gln Ile
            35                  40

<210> SEQ ID NO 43
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr-anchor-linker
<220> FEATURE:
<223> OTHER INFORMATION: C-term amidated

<400> SEQUENCE: 43

Thr Arg Phe Thr Leu Ser Leu Asp Val Pro Thr Asn Ile Met Asn Leu
1               5                   10                  15

Leu Phe Asn Ile Ala Lys Ala Arg Asn Leu Arg Ala Gln Ala Ala Ala
            20                  25                  30

Asn Ala His Leu Met Ala Gln Ile
            35                  40

<210> SEQ ID NO 44
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr-anchor-linker
<220> FEATURE:
<223> OTHER INFORMATION: C-term amidated

<400> SEQUENCE: 44

Thr Lys Phe Thr Leu Ser Leu Asp Val Pro Thr Asn Ile Met Asn Leu
1               5                   10                  15

Leu Phe Asn Ile Ala Arg Ala Arg Asn Leu Arg Ala Gln Ala Ala Ala
            20                  25                  30

Asn Ala His Leu Met Ala Gln Ile
            35                  40

```
<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr-anchor-linker
<220> FEATURE:
<223> OTHER INFORMATION: C-term amidated

<400> SEQUENCE: 45

Thr Arg Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
            35                  40

<210> SEQ ID NO 46
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr-anchor-linker
<220> FEATURE:
<223> OTHER INFORMATION: C-term amidated

<400> SEQUENCE: 46

Thr Lys Phe Thr Leu Ser Leu Asp Val Pro Thr Asn Ile Met Asn Leu
1               5                   10                  15

Leu Phe Asn Ile Ala Arg Ala Lys Asn Leu Arg Ala Gln Ala Ala Ala
            20                  25                  30

Asn Ala His Leu Met Ala Gln Ile
            35                  40

<210> SEQ ID NO 47
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr-anchor-linker
<220> FEATURE:
<223> OTHER INFORMATION: C-term amidated

<400> SEQUENCE: 47

Thr Lys Phe Thr Leu Ser Leu Asp Val Pro Thr Asn Ile Met Asn Leu
1               5                   10                  15

Leu Phe Asn Ile Ala Lys Ala Arg Asn Leu Arg Ala Gln Ala Ala Ala
            20                  25                  30

Asn Ala His Leu Met Ala Gln Ile
            35                  40

<210> SEQ ID NO 48
```

```
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys-epsilon-linker-anchor
<220> FEATURE:
<223> OTHER INFORMATION: C-term amidated

<400> SEQUENCE: 48

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
            35                  40

<210> SEQ ID NO 49
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys-epsilon-linker-anchor
<220> FEATURE:
<223> OTHER INFORMATION: C-term amidated

<400> SEQUENCE: 49

Thr Lys Phe Thr Leu Ser Leu Asp Val Pro Thr Asn Ile Met Asn Leu
1               5                   10                  15

Leu Phe Asn Ile Ala Arg Ala Lys Asn Leu Arg Ala Gln Ala Ala Ala
            20                  25                  30

Asn Ala His Leu Met Ala Gln Ile
            35                  40

<210> SEQ ID NO 50
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys-epsilon-linker-anchor
<220> FEATURE:
<223> OTHER INFORMATION: C-term amidated

<400> SEQUENCE: 50

Thr Lys Phe Thr Leu Ser Leu Asp Val Pro Thr Asn Ile Met Asn Leu
1               5                   10                  15

Leu Phe Asn Ile Ala Lys Ala Arg Asn Leu Arg Ala Gln Ala Ala Ala
            20                  25                  30

Asn Ala His Leu Met Ala Gln Ile
            35                  40

<210> SEQ ID NO 51
<211> LENGTH: 40
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys-epsilon-linker-anchor
<220> FEATURE:
<223> OTHER INFORMATION: C-term amidated

<400> SEQUENCE: 51

Thr Lys Phe Thr Leu Ser Leu Asp Val Pro Thr Asn Ile Met Asn Leu
1               5                   10                  15

Leu Phe Asn Ile Ala Arg Ala Arg Asn Leu Arg Ala Gln Ala Ala Ala
            20                  25                  30

Asn Ala His Leu Met Ala Gln Ile
            35                  40

<210> SEQ ID NO 52
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-linker-anchor
<220> FEATURE:
<223> OTHER INFORMATION: C-term amidated

<400> SEQUENCE: 52

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
            35                  40

<210> SEQ ID NO 53
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-linker-anchor
<220> FEATURE:
<223> OTHER INFORMATION: C-term amidated

<400> SEQUENCE: 53

Thr Arg Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
            35                  40

<210> SEQ ID NO 54
<211> LENGTH: 40
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-linker-anchor
<220> FEATURE:
<223> OTHER INFORMATION: C-term amidated

<400> SEQUENCE: 54

Thr Lys Phe Thr Leu Ser Leu Asp Val Pro Thr Asn Ile Met Asn Leu
1               5                   10                  15

Leu Phe Asn Ile Ala Lys Ala Arg Asn Leu Arg Ala Gln Ala Ala Ala
            20                  25                  30

Asn Ala His Leu Met Ala Gln Ile
        35                  40

<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-linker-anchor
<220> FEATURE:
<223> OTHER INFORMATION: C-term amidated

<400> SEQUENCE: 55

Thr Arg Phe Thr Leu Ser Leu Asp Val Pro Thr Asn Ile Met Asn Leu
1               5                   10                  15

Leu Phe Asn Ile Ala Lys Ala Arg Asn Leu Arg Ala Gln Ala Ala Ala
            20                  25                  30

Asn Ala His Leu Met Ala Gln Ile
        35                  40

<210> SEQ ID NO 56
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Lys-epsilon-linker-anchor
<220> FEATURE:
<223> OTHER INFORMATION: C-term amidated

<400> SEQUENCE: 56

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (24)..(24)
<223> OTHER INFORMATION: Lys-epsilon-linker-anchor
<220> FEATURE:
<223> OTHER INFORMATION: C-term amidated

<400> SEQUENCE: 57

Thr Arg Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile
        35                  40

<210> SEQ ID NO 58
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Lys-epsilon-linker-anchor
<220> FEATURE:
<223> OTHER INFORMATION: C-term amidated

<400> SEQUENCE: 58

Thr Lys Phe Thr Leu Ser Leu Asp Val Pro Thr Asn Ile Met Asn Leu
1               5                   10                  15

Leu Phe Asn Ile Ala Arg Ala Lys Asn Leu Arg Ala Gln Ala Ala Ala
            20                  25                  30

Asn Ala His Leu Met Ala Gln Ile
        35                  40

<210> SEQ ID NO 59
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Lys-epsilon-linker-anchor
<220> FEATURE:
<223> OTHER INFORMATION: C-term amidated

<400> SEQUENCE: 59

Thr Arg Phe Thr Leu Ser Leu Asp Val Pro Thr Asn Ile Met Asn Leu
1               5                   10                  15

Leu Phe Asn Ile Ala Arg Ala Lys Asn Leu Arg Ala Gln Ala Ala Ala
            20                  25                  30

Asn Ala His Leu Met Ala Gln Ile
        35                  40

<210> SEQ ID NO 60
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (27)..(27)
<223> OTHER INFORMATION: Lys-epsilon-linker-anchor
<220> FEATURE:
<223> OTHER INFORMATION: C-term amidated

<400> SEQUENCE: 60

Thr Lys Phe Thr Leu Ser Leu Asp Val Pro Thr Asn Ile Met Asn Leu
1               5                   10                  15

Leu Phe Asn Ile Ala Lys Ala Lys Asn Leu Lys Ala Gln Ala Ala Ala
            20                  25                  30

Asn Ala His Leu Met Ala Gln Ile
        35                  40

<210> SEQ ID NO 61
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor
<220> FEATURE:
<223> OTHER INFORMATION: C-term amidated

<400> SEQUENCE: 61

Thr Arg Phe Thr Leu Ser Leu Asp Val Pro Thr Asn Ile Met Asn Leu
1               5                   10                  15

Leu Phe Asn Ile Ala Arg Ala Arg Asn Leu Lys Ala Gln Ala Ala Ala
            20                  25                  30

Asn Ala His Leu Met Ala Gln Ile
        35                  40

<210> SEQ ID NO 62
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor
<220> FEATURE:
<223> OTHER INFORMATION: C-term amidated

<400> SEQUENCE: 62

Thr Arg Phe Thr Leu Ser Leu Asp Val Pro Thr Asn Ile Met Asn Leu
1               5                   10                  15

Leu Phe Asn Ile Ala Arg Ala Lys Asn Leu Lys Ala Gln Ala Ala Ala
            20                  25                  30

Asn Ala His Leu Met Ala Gln Ile
        35                  40

<210> SEQ ID NO 63
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor

```
<220> FEATURE:
<223> OTHER INFORMATION: C-term amidated

<400> SEQUENCE: 63

Thr Arg Phe Thr Leu Ser Leu Asp Val Pro Thr Asn Ile Met Asn Leu
1               5                   10                  15

Leu Phe Asn Ile Ala Lys Ala Arg Asn Leu Lys Ala Gln Ala Ala Ala
                20                  25                  30

Asn Ala His Leu Met Ala Gln Ile
            35                  40

<210> SEQ ID NO 64
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor
<220> FEATURE:
<223> OTHER INFORMATION: C-term amidated

<400> SEQUENCE: 64

Thr Lys Phe Thr Leu Ser Leu Asp Val Pro Thr Asn Ile Met Asn Leu
1               5                   10                  15

Leu Phe Asn Ile Ala Arg Ala Arg Asn Leu Lys Ala Gln Ala Ala Ala
                20                  25                  30

Asn Ala His Leu Met Ala Gln Ile
            35                  40

<210> SEQ ID NO 65
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor
<220> FEATURE:
<223> OTHER INFORMATION: C-term amidated

<400> SEQUENCE: 65

Thr Arg Phe Thr Leu Ser Leu Asp Val Pro Thr Asn Ile Met Asn Leu
1               5                   10                  15

Leu Phe Asn Ile Ala Lys Ala Lys Asn Leu Lys Ala Gln Ala Ala Ala
                20                  25                  30

Asn Ala His Leu Met Ala Gln Ile
            35                  40

<210> SEQ ID NO 66
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor
<220> FEATURE:
<223> OTHER INFORMATION: C-term amidated
```

```
<400> SEQUENCE: 66

Thr Lys Phe Thr Leu Ser Leu Asp Val Pro Thr Asn Ile Met Asn Leu
1               5                   10                  15

Leu Phe Asn Ile Ala Arg Ala Lys Asn Leu Lys Ala Gln Ala Ala Ala
                20                  25                  30

Asn Ala His Leu Met Ala Gln Ile
            35                  40

<210> SEQ ID NO 67
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys-epsilon-linker-anchor
<220> FEATURE:
<223> OTHER INFORMATION: C-term amidated

<400> SEQUENCE: 67

Thr Lys Phe Thr Leu Ser Leu Asp Val Pro Thr Asn Ile Met Asn Leu
1               5                   10                  15

Leu Phe Asn Ile Ala Lys Ala Arg Asn Leu Lys Ala Gln Ala Ala Ala
                20                  25                  30

Asn Ala His Leu Met Ala Gln Ile
            35                  40

<210> SEQ ID NO 68
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 68

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
                20                  25                  30

Asn Ala His Leu Met Ala Gln Ile Lys
            35                  40

<210> SEQ ID NO 69
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 69
```

Thr Arg Phe Thr Leu Ser Leu Asp Val Pro Thr Asn Ile Met Asn Leu
1               5                   10                  15

Leu Phe Asn Ile Ala Arg Ala Arg Asn Leu Arg Ala Gln Ala Ala Ala
                20                  25                  30

Asn Ala His Leu Met Ala Gln Ile Lys
            35                  40

<210> SEQ ID NO 70
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 70

Thr Arg Phe Thr Leu Ser Leu Asp Val Pro Thr Asn Ile Met Asn Leu
1               5                   10                  15

Leu Phe Asn Ile Ala Arg Ala Lys Asn Leu Arg Ala Gln Ala Ala Ala
                20                  25                  30

Asn Ala His Leu Met Ala Gln Ile Lys
            35                  40

<210> SEQ ID NO 71
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 71

Thr Arg Phe Thr Leu Ser Leu Asp Val Pro Thr Asn Ile Met Asn Leu
1               5                   10                  15

Leu Phe Asn Ile Ala Lys Ala Arg Asn Leu Arg Ala Gln Ala Ala Ala
                20                  25                  30

Asn Ala His Leu Met Ala Gln Ile Lys
            35                  40

<210> SEQ ID NO 72
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 72

Thr Lys Phe Thr Leu Ser Leu Asp Val Pro Thr Asn Ile Met Asn Leu

```
 1               5                   10                  15
Leu Phe Asn Ile Ala Arg Ala Arg Asn Leu Arg Ala Gln Ala Ala Ala
            20                  25                  30

Asn Ala His Leu Met Ala Gln Ile Lys
            35                  40

<210> SEQ ID NO 73
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 73

Thr Arg Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
            20                  25                  30

Asn Ala His Leu Met Ala Gln Ile Lys
            35                  40

<210> SEQ ID NO 74
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 74

Thr Lys Phe Thr Leu Ser Leu Asp Val Pro Thr Asn Ile Met Asn Leu
1               5                   10                  15

Leu Phe Asn Ile Ala Arg Ala Lys Asn Leu Arg Ala Gln Ala Ala Ala
            20                  25                  30

Asn Ala His Leu Met Ala Gln Ile Lys
            35                  40

<210> SEQ ID NO 75
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (41)..(41)
<223> OTHER INFORMATION: Lys-epsilon-linker-anchor
<220> FEATURE:
<223> OTHER INFORMATION: C-term amidated

<400> SEQUENCE: 75

Thr Lys Phe Thr Leu Ser Leu Asp Val Pro Thr Asn Ile Met Asn Leu
1               5                   10                  15
```

Leu Phe Asn Ile Ala Lys Ala Arg Asn Leu Arg Ala Gln Ala Ala Ala
                20                  25                  30

Asn Ala His Leu Met Ala Gln Ile Lys
                35                  40

<210> SEQ ID NO 76
<211> LENGTH: 38
<212> TYPE: PRT
<213> ORGANISM: Homo sapiens
<220> FEATURE:
<223> OTHER INFORMATION: C-term amidated

<400> SEQUENCE: 76

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
                20                  25                  30

Arg Ile Leu Ala Arg Val
                35

<210> SEQ ID NO 77
<211> LENGTH: 38
<212> TYPE: PRT
<213> ORGANISM: Homo sapiens
<220> FEATURE:
<223> OTHER INFORMATION: C-term amidated

<400> SEQUENCE: 77

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
                20                  25                  30

His Leu Met Ala Gln Ile
                35

<210> SEQ ID NO 78
<211> LENGTH: 43
<212> TYPE: PRT
<213> ORGANISM: Homo sapiens
<220> FEATURE:
<223> OTHER INFORMATION: C-term amidated

<400> SEQUENCE: 78

His Pro Gly Ser Arg Ile Val Leu Ser Leu Asp Val Pro Ile Gly Leu
1               5                   10                  15

Leu Gln Ile Leu Leu Glu Gln Ala Arg Ala Arg Ala Ala Arg Glu Gln
                20                  25                  30

Ala Thr Thr Asn Ala Arg Ile Leu Ala Arg Val
                35                  40

<210> SEQ ID NO 79
<211> LENGTH: 40
<212> TYPE: PRT
<213> ORGANISM: Homo sapiens
<220> FEATURE:
<223> OTHER INFORMATION: C-term amidated

<400> SEQUENCE: 79

Thr Lys Phe Thr Leu Ser Leu Asp Val Pro Thr Asn Ile Met Asn Leu
1               5                   10                  15

Leu Phe Asn Ile Ala Lys Ala Lys Asn Leu Arg Ala Gln Ala Ala Ala
                20                  25                  30

Asn Ala His Leu Met Ala Gln Ile

```
          35                  40

<210> SEQ ID NO 80
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-AEEA-MPA
<220> FEATURE:
<223> OTHER INFORMATION: C-term amidated

<400> SEQUENCE: 80

Asp Asn Pro Ser Leu Ser Ile Asp Leu Thr Phe His Leu Leu Arg Thr
1               5                   10                  15

Leu Leu Glu Leu Ala Lys Thr Gln Ser Gln Arg Glu Arg Ala Glu Gln
            20                  25                  30

Asn Arg Ile Ile Phe Asp Ser Val
        35                  40

<210> SEQ ID NO 81
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile-MPA-AEEA
<220> FEATURE:
<223> OTHER INFORMATION: C-term amidated

<400> SEQUENCE: 81

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 82
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Lys-epsilon-AEEA-MPA
<220> FEATURE:
<223> OTHER INFORMATION: C-term amidated

<400> SEQUENCE: 82

Ile Val Leu Ser Leu Asp Val Pro Ile Gly Leu Leu Gln Ile Leu Leu
1               5                   10                  15

Glu Gln Ala Lys Ala Arg Ala Ala Arg Glu Gln Ala Thr Thr Asn Ala
            20                  25                  30

Arg Ile Leu Ala Arg Val
        35
```

<210> SEQ ID NO 83
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-AEEA-MPA
<220> FEATURE:
<223> OTHER INFORMATION: C-term amidated

<400> SEQUENCE: 83

Ile Val Leu Ser Leu Asp Val Pro Ile Gly Leu Leu Gln Ile Leu Leu
1               5                   10                  15

Glu Gln Ala Arg Ala Lys Ala Ala Arg Glu Gln Ala Thr Thr Asn Ala
            20                  25                  30

Arg Ile Leu Ala Arg Val
        35

<210> SEQ ID NO 84
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Lys-epsilon-AEEA-MPA
<220> FEATURE:
<223> OTHER INFORMATION: C-term amidated

<400> SEQUENCE: 84

Ile Val Leu Ser Leu Asp Val Pro Ile Gly Leu Leu Gln Ile Leu Leu
1               5                   10                  15

Glu Gln Ala Arg Ala Arg Ala Ala Lys Glu Gln Ala Thr Thr Asn Ala
            20                  25                  30

Arg Ile Leu Ala Arg Val
        35

<210> SEQ ID NO 85
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Lys-epsilon-AEEA-MPA
<220> FEATURE:
<223> OTHER INFORMATION: C-term amidated

<400> SEQUENCE: 85

Phe Thr Leu Ser Leu Asp Val Pro Thr Asn Ile Met Asn Leu Leu Phe
1               5                   10                  15

Asn Ile Ala Lys Ala Arg Asn Leu Arg Ala Gln Ala Ala Ala Asn Ala
            20                  25                  30

His Leu Met Ala Gln Ile
        35

<210> SEQ ID NO 86

```
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-AEEA-MPA residue-albumin
<220> FEATURE:
<223> OTHER INFORMATION: C-term amidated

<400> SEQUENCE: 86

Asp Asn Pro Ser Leu Ser Ile Asp Leu Thr Phe His Leu Leu Arg Thr
1               5                   10                  15

Leu Leu Glu Leu Ala Lys Thr Gln Ser Gln Arg Glu Arg Ala Glu Gln
            20                  25                  30

Asn Arg Ile Ile Phe Asp Ser Val
        35                  40

<210> SEQ ID NO 87
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile-albumin-MPA residue-AEEA
<220> FEATURE:
<223> OTHER INFORMATION: C-term amidated

<400> SEQUENCE: 87

Ile Val Leu Ser Leu Asp Val Pro Ile Gly Leu Leu Gln Ile Leu Leu
1               5                   10                  15

Glu Gln Ala Arg Ala Arg Ala Arg Glu Gln Ala Thr Thr Asn Ala
            20                  25                  30

Arg Ile Leu Ala Arg Val
        35

<210> SEQ ID NO 88
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Lys-epsilon-AEEA-MPA residue-albumin
<220> FEATURE:
<223> OTHER INFORMATION: C-term amidated

<400> SEQUENCE: 88

Ile Val Leu Ser Leu Asp Val Pro Ile Gly Leu Leu Gln Ile Leu Leu
1               5                   10                  15

Glu Gln Ala Lys Ala Arg Ala Ala Arg Glu Gln Ala Thr Thr Asn Ala
            20                  25                  30

Arg Ile Leu Ala Arg Val
        35

<210> SEQ ID NO 89
<211> LENGTH: 38
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Lys-epsilon-AEEA-MPA residue-albumin
<220> FEATURE:
<223> OTHER INFORMATION: C-term amidated

<400> SEQUENCE: 89

Ile Val Leu Ser Leu Asp Val Pro Ile Gly Leu Leu Gln Ile Leu Leu
1               5                   10                  15

Glu Gln Ala Arg Ala Lys Ala Ala Arg Glu Gln Ala Thr Thr Asn Ala
            20                  25                  30

Arg Ile Leu Ala Arg Val
        35

<210> SEQ ID NO 90
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Lys-epsilon-AEEA-MPA residue-albumin
<220> FEATURE:
<223> OTHER INFORMATION: C-term amidated

<400> SEQUENCE: 90

Ile Val Leu Ser Leu Asp Val Pro Ile Gly Leu Leu Gln Ile Leu Leu
1               5                   10                  15

Glu Gln Ala Arg Ala Arg Ala Ala Lys Glu Gln Ala Thr Thr Asn Ala
            20                  25                  30

Arg Ile Leu Ala Arg Val
        35

<210> SEQ ID NO 91
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Lys-epsilon-AEEA-MPA residue-albumin
<220> FEATURE:
<223> OTHER INFORMATION: C-term amidated

<400> SEQUENCE: 91

Phe Thr Leu Ser Leu Asp Val Pro Thr Asn Ile Met Asn Leu Leu Phe
1               5                   10                  15

Asn Ile Ala Lys Ala Arg Asn Leu Arg Ala Gln Ala Ala Ala Asn Ala
            20                  25                  30

His Leu Met Ala Gln Ile
        35

<210> SEQ ID NO 92
<211> LENGTH: 41
<212> TYPE: PRT
<213> ORGANISM: Homo sapiens
<220> FEATURE:

-continued

```
<223> OTHER INFORMATION: C-term amidated

<400> SEQUENCE: 92

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val Gly His Cys
        35                  40
```

US 7,982,018 B2

MODIFIED CORTICOTROPIN RELEASING FACTOR PEPTIDES AND USES THEREOF

CROSS-REFERENCE TO RELATED APPLICATIONS

This application claims priority to U.S. Application Ser. No. 60/852,443, filed on Oct. 16, 2006 and U.S. Application Ser. No. 60/967,281, filed on Aug. 30, 2007. The disclosures of the prior applications are considered part of (and are incorporated by reference in) the disclosure of this application.

FIELD OF THE INVENTION

The present invention relates to modified peptides and conjugates of the corticotropin releasing factor family, specifically modified urocortin and urocortin-related peptides, and methods of making and using the modified peptides and conjugates.

BACKGROUND

Urocortin peptides are members of the corticotropin releasing factor ("CRF", also called corticotrophin releasing factor) family. Urocortin and urocortin-related peptides include urocortin 1, urocortin 2, urocortin 3, stresscopin-related peptide (SRP), and stresscopin (SCP). These peptides have biological activity in various physiological systems. For example, urocortin has been shown to decrease food intake in mice by the CRF type 2 receptor. Asakawa et al., *Gastroenterology* 1999, 116:1287-1292.

Modified urocortin peptides having improved pharmacokinetic properties, particularly a decreased rate of excretion and/or increased circulating half life as compared to urocortin peptides, are needed for the treatment and prevention of diseases or disorders that can be treated or prevented by the administration of urocortin or urocortin-related peptides.

SUMMARY

The present disclosure provides a compound comprising a modified CRF peptide, or a modified derivative thereof, wherein the peptide or derivative is modified by the covalent attachment of a reactive group to the peptide or derivative, wherein the covalent attachment is optionally through a linking group, and wherein the reactive group is capable of forming a covalent bond with an amino, hydroxyl, or thiol group of a serum protein. In a specific embodiment of all aspects of the invention described herein, the CRF is a modified urocortin or urocortin-related peptide or modified derivative thereof.

The present disclosure also provides a conjugate comprising a modified CRF peptide, or a modified derivative thereof, wherein the peptide or derivative is modified by the covalent attachment of a reactive group, optionally through a linking group, to the peptide or derivative, and wherein the reactive group is covalently attached to a serum protein. Preferably, the modified CRF peptide is urocortin or urocortin related peptide or a modified derivative thereof.

The present disclosure thus provides modified peptides of the CRF family, modified derivatives thereof, and conjugates of such modified peptides and derivatives to blood components, preferably serum proteins or peptides. The modified peptides, or derivatives thereof, are urocortin or urocortin-related peptides and their derivatives as more fully described in Section I. In certain embodiments, a urocortin or urocortin-related peptide is selected from the group consisting of urocortin 1, urocortin 2, urocortin 3, stresscopin-related peptide (SRP), and stresscopin (SCP). The urocortin can be urocortin 1 as provided in SEQ ID NO:1, urocortin 2 as provided in SEQ ID NOs: 76 and 92, or urocortin 3 as provided in SEQ ID NO:77. The urocortin-related peptide can be SRP as provided in SEQ ID NO: 78 or SCP as provided in SEQ ID NO:79.

The peptides of the invention are modified by the covalent attachment of one or more reactive groups to the peptide. Preferably, each peptide is modified by the covalent attachment of one reactive group to a defined amino acid of the peptide. A reactive group is chosen for its ability to form a covalent bond with another peptide or protein, thus enabling the covalent attachment of the modified peptide to the other peptide or protein through the reactive group. Preferably, the reactive group forms a covalent bond with a peptide or protein present in blood, referred to herein as a serum protein or peptide. As used herein, reference to blood or serum proteins (or peptides) mean that the protein or peptide can be found in the blood or serum but for purposes of the invention need not be isolated from the blood or serum. Thus, a blood or serum protein (or peptide) as used herein can be chemically synthesized or recombinantly produced. In a specific embodiment, the serum protein is albumin, transferrin, ferritin, an immunoglobulin such as IgM or IgG a steroid binding protein, a thyroxin binding protein, or an alpha-2-macroglobulin. In one embodiment, the serum protein is recombinant. In a preferred embodiment, the serum protein is recombinantly produced albumin, preferably recombinant human albumin.

The present disclosure also provides conjugates that are composed of modified peptides that are covalently attached to a serum protein through the reactive group. Thus, a conjugate of the present invention comprises a modified urocortin or urocortin-related peptide, or a modified derivative thereof, in which the reactive group has formed a covalent bond to a serum protein. In one embodiment of the conjugate, the serum protein is selected from the group consisting of albumin, transferrin, ferritin, IgM, IgG, a steroid binding protein, a thyroxin binding protein, and alpha-2-macroglobulin.

In one embodiment of the compound or conjugate, the covalent attachment of the reactive group is at substantially only one site on the peptide or derivative.). In one embodiment, the reactive group, e.g., maleimide group, is attached at the N-terminus of the peptide or the C-terminus of the peptide. In one embodiment, the reactive group is attached to at an ε-amino a group of a lysine present in the amino acid sequence of the peptide. In one embodiment, one or more lysine present in the amino acid sequence of the peptide is deleted or substituted to a non-lysine amino acid residue within the peptide sequence. In some embodiments, a lysine residue that can be attached with the reactive group, e.g., the maleimide group, is added to the peptide sequence, e.g., inserted or substituting a non-lysine residue in the peptide. In some embodiments, the amino acid sequence of the peptide has been modified so that only one lysine is present in the amino acid sequence of the peptide.

In one embodiment of the conjugate, the covalent attachment of the reactive group is at substantially only one site on the peptide or derivative and the reactive group is covalently attached to the serum protein at substantially only one site on the serum protein. In a preferred embodiment, the serum protein is albumin. In a specific embodiment, the covalent attachment of the reactive group is at the epsilon amino group of a lysine in the peptide or derivative, optionally through a linking group, and the reactive group is covalently attached to albumin through a maleimide group to the thiol group of cysteine 34 of albumin. The maleimide group can be part of a gamma-maleimide butyrylamide (GMBA) or a maleimido propionic acid (MPA).

In one embodiment of the compound, the reactive group can covalently attach to albumin, preferably human albumin. In one embodiment of the conjugate, the reactive group is covalently attached to albumin, preferably human albumin. In one embodiment, the serum protein is recombinant, preferably recombinant albumin, and most preferably recombinant human albumin.

In one embodiment of the compound or conjugate, the reactive group is a maleimide containing group, preferably GMBA or MPA.

In one embodiment of the compound or conjugate, the peptide or derivative is covalently attached to the reactive group through one or more linking groups. Preferably, the one or more linking groups is selected from the group consisting of AEA ((2-amino) ethoxy acetic acid), AEEA ([2-(2-amino) ethoxy)]ethoxy acetic acid), or OA (8-amino octanoic acid, also called 8-amino caprylic acid, of formula $NH_2$—$(CH_2)_7$—COOH). In a specific example of the embodiment in which there is more than one linking group, each linking group can be independently selected from the group consisting of AEA ((2-amino) ethoxy acetic acid), AEEA ([2-(2-amino)ethoxy)]ethoxy acetic acid), and OA (8-amino octanoic acid). In a specific embodiment, the linking group is $(AEEA)_n$ where n is 0, 1, 2, 3, 4, 5, or 6. In another specific embodiment, the linking group is $(OA)_n$ where n is 0, 1, 2, 3, 4, 5, or 6. In a further specific embodiment, the linking group is $(AEA)_n$ where n is 0, 1, 2, 3, 4, 5, or 6. In certain embodiments, the linking group is a peptide having a labile chemical bond which is cleavable by an enzyme or which is cleaved under acidic conditions.

In one embodiment of the compound or conjugate, the peptide is selected from the group consisting of urocortin 1, urocortin 2, urocortin 3, SRP, and SCP. The urocortin can be urortin 1 as provided in SEQ ID NO: 1, urocortin 2 as provided in SEQ ID NOs: 76 and 92, or urocortin 3 as provided in SEQ ID NO:77. The urocortin-related peptide can be SRP as provided in SEQ ID NO: 78 or SCP as provided in SEQ ID NO:79.

In one embodiment of the compound or conjugate, the derivative has up to 4 amino acid substitutions, insertions, or deletions relative to the sequence of the peptide.

In one embodiment of the compound or conjugate, the derivative has up to but not more than 4 amino acid substitutions, insertions or deletions relative to the sequence of urocortin 1, urocortin 2, urocortin 3, stresscopin-related peptide (SRP) and stresscopin (SCP), e.g., the amino acid sequence of SEQ ID NOs:1, 76, 92, 77, 78 or 79.

In one embodiment of the compound or conjugate, the peptide or derivative is selected from the group consisting of SEQ ID NOS:1-85 and 92.

In one embodiment of the compound or conjugate, the peptide or derivative is a mammalian peptide or derivative. In one embodiment, the peptide or derivative is selected from the group consisting of a mouse, rat, guinea pig, rabbit, dog, horse, cow, pig, or primate peptide or derivative. In a preferred embodiment, the peptide or derivative is a human peptide or derivative.

In one embodiment of the conjugate, the conjugate has a decreased rate of excretion and/or an increased circulating half-life in vivo and/or decreased toxicity profile (e.g., decreased effects associated with binding of central nervous system receptors) as compared to a corresponding unconjugated peptide. In one embodiment, the conjugate retains at least some of the biological activity of the unconjugated peptide. In another embodiment, the conjugate exhibits more biological activity than the unconjugated peptide. In certain embodiments, the biological activity is the ability to modulate arousal, anxiety, cognitive functions, appetite, food intake, nutrient availability. In certain embodiments, the biological activity is the ability to bind to a corticotropin releasing factor type I or type II receptor ("CRFR1" or "CRFR2") or a member of its family of subtypes. In certain embodiments, the biological activity is the ability to bind both CRFR1 and CRFR2, e.g., the ability to bind both CRFR1 and CRFR2 but preferentially binds to CRFR1 or the ability to bind both CRFR1 and CRFR2 but preferentially binds CRFR2. In certain embodiments, the biological activity is the ability to modulate one or more of body weight (weight gain or weigh loss), food intake, appetite, nutrient availability, gastric emptying, gastric acid secretion and regulation of glycemic control. In certain embodiments, the biological activity is hypotensive activity, the ability to increase coronary blood flow, increase vasodilation and/or cardiac intropic effects. In certain embodiments, the biological activity is ischemia reperfusion injury and the ability to decrease ischemia reperfusion injury. In certain embodiments, the biological activity is muscle atrophy or the ability to modulate muscle mass through increase or hypertrophy or through decreased loss from atrophy or wasting.

In one embodiment of the conjugate, the conjugate is selected from the group consisting of SEQ ID NOS:86-91.

The present invention also provides methods for the covalent attachment of a modified peptide to a serum protein to form a conjugate with a serum protein. In one embodiment, the compound or conjugate is a compound or conjugate described herein.

In one embodiment, a modified peptide is covalently bound to a serum protein in vitro (ex vivo), by an in vitro reaction of the serum protein with the modified peptide comprising the reactive group, such that the modified peptide is covalently attached to the serum protein through the reactive group. In another embodiment, a modified peptide is covalently bound to a serum protein in vivo, by an in vivo reaction of the serum protein with the modified peptide comprising the reactive group, such that the modified peptide is covalently attached to the serum protein through the reactive group.

The disclosure also provides a method for extending the in vivo half-life of a modified peptide e.g., a modified peptide described herein, the method comprises contacting the modified peptide with a serum protein under conditions suitable for the formation of a covalent bond between the reactive group and a serum protein, thereby forming a modified peptide conjugated to the serum protein, which modified peptide conjugated to the serum protein has an increased in vivo half-life relative to the unconjugated modified peptide. In one embodiment, the contacting is performed in vivo.

In one embodiment, the contacting is performed in vitro (e.g., ex vivo). In a preferred embodiment, the serum protein is albumin, preferably human, e.g., recombinant human albumin.

The disclosure also provides a method for modifying the biological activity of a urocortin or urocortin-related peptide e.g., a modified urocortin or urocortin-related peptide described herein, by forming a conjugate with a serum protein, e.g., a conjugate described herein, either in vivo by administration of a compound (comprising a modified peptide or modified derivative with a reactive group as described above) or forming a conjugate in vitro (e.g., ex vivo), as described herein. For example, the biological activity can be modified by separating the action on peripheral nervous system receptors (e.g., non-central nervous system receptors anywhere else in the body) and central nervous system receptors following the formation of a covalent bond between the reactive group and the serum protein. In one embodiment, the method allows access of the conjugate of the invention to peripheral receptors only so as to directly act in an agonist or antagonist manner.

The disclosure also provides a method for modifying the biological activity of a urocortin or urocortin-related peptide by forming a conjugate e.g., a conjugate described herein, either in vivo by administration of a compound (comprising a modified peptide or modified derivative with a reactive group as described above) or forming a conjugate in vitro (e.g., ex vivo), as described herein, for example, by modifying or fully separating the affinity or specificity for the different urocortin-binding receptors. In one embodiment, the conjugate of the invention has a greater affinity or specificity toward CRFR2 than CRFR1, which is different or opposite from the unmodified peptide. In another embodiment, the conjugate has a greater affinity or specificity toward CRFR1 than CRFR2, which is different or opposite from the unmodified peptide. In a further embodiment, the conjugate has a different affinity or specificity profile toward the family of CRF receptors than the unmodified peptide, without changing the global preference toward one family as seen with the unmodified peptide.

The disclosure also provides a method for treating or preventing a disease or disorder in a subject, the method comprises administering to the subject an amount of the compound or conjugate e.g., a compound or conjugate described herein, effective for said treating or preventing. In one embodiment, the disease or disorder is a cardiovascular disease or disorder (e.g., atherosclerosis, hypertension, dyslipidemia, etc). In a specific embodiment, the cardiovascular disease or disorder is acute decompensated heart failure (ADHF) or congestive heart failure (CHF). In another specific embodiment, the compound or conjugate is administered to at least provide cardiovascular protection, for example, following myocardial ischemia/infarction (MI) or cardiovascular surgery. In one embodiment, the disease or disorder is stress or anxiety. In some embodiments, the disorder is hypertension and dyslipidemia. In one embodiment, the disorder is a memory or learning disorder. In one embodiment, the disease or disorder is an appetite disease or disorder. In one embodiment, the disorder is a disorder which can be treated by one or more of: reducing food intake, reducing nutrient availability, reducing appetite, or reducing weight gain or increasing weight loss. Exemplary disorders include: insulin resistant subjects, glucose intolerant subjects, or subjects having diabetes mellitus (e.g., type 1,2 or gestational diabetes) or manifestations of insulin resistance syndrome (e.g., Syndrome X). In a specific embodiment, the appetite disease or disorder is an eating disorder such as, e.g., obesity or anorexia. In one embodiment, the disease or disorder is a physiologic disorder selected from abnormal body temperature, abnormal levels of corticotropin releasing factor (CRF), and abnormal levels of adreno corticotropic hormone (ACTH). In one embodiment, the disorder is a disorder associated with muscle atrophy or through decreased loss from atrophy or wasting (e.g., Duschenne muscular dystrophy and Becker muscular dystrophy). In a preferred embodiment, the subject is human.

The disclosure also provides a method of decreasing one or more of body weight (weight gain or weight loss), body mass index, nutrient availability, appetite and food intake in a subject, the method comprises administering to the subject an amount of a compound or conjugate described herein effective to decrease one or more of body weight and food intake. The disclosure also provides a method of increasing one or more of gastric emptying and regulation of glycemic control in a subject, the method comprises administering to the subject an amount of a compound or conjugate described herein effective to increase gastric emptying, gastric acid secretion and/or regulation of glycemic control.

The disclosure also provides a method of modulating muscle mass through increase or hypertrophy or through decreased loss from atrophy or wasting. The method comprises administering to the subject an amount of a compound or conjugate described herein effective to modulate muscle mass through increase or hypertrophy or through decreased loss from atrophy or wasting.

Also included in the disclosure is a method of modulating hypotensive activity, the ability to increase coronary blood flow or left ventricular ejection fraction, and the ability to decrease vascular resistance or renal function. The method comprises administering to the subject an amount of a compound or conjugate described herein effective to modulate hypotensive activity, the increase coronary blood flow or left ventricular ejection fraction, and to decrease vascular resistance or renal function.

The invention also provides a pharmaceutical composition comprising a compound or conjugate described herein and one or more of a pharmaceutically acceptable carrier, excipient, and diluent.

In a specific embodiment, the compounds or conjugates described herein are purified. In a specific embodiment, the compounds or conjugates of the invention that are used in the methods described herein and/or that are present in the pharmaceutical compositions described herein.

The invention also provides a kit comprising in one or more containers a compound or conjugate described herein. In one embodiment, the compound or conjugate is in lyophilized form. In accordance with this embodiment, the kit further comprises a container of sterile solution suitable for reconstituting the lyophilized compound or conjugate.

The invention also provides a container, e.g., a syringe, containing in a solution a compound or conjugate described herein.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
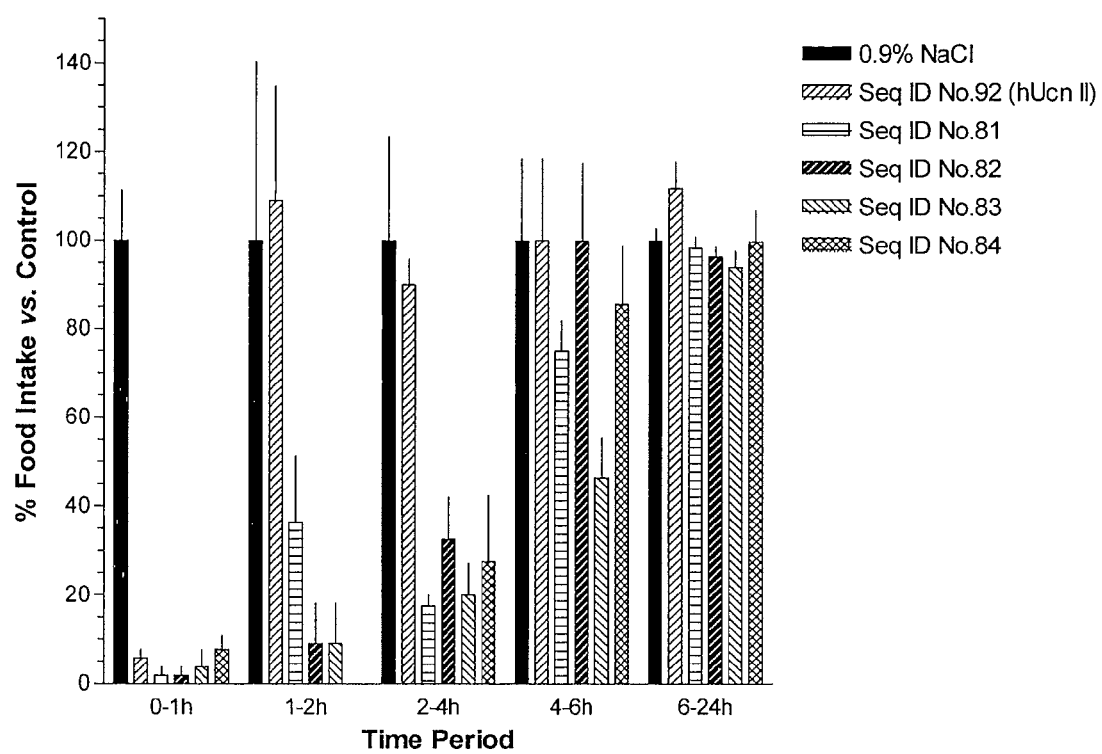
FIG. 1 is a graph depicting the effect of human urocortin 2 derivatives on food intake in normal mice. Compounds were injected intravenously at 85 nmol/kg. Results are expressed as mean ±SE of 4 cages per group (n=3 mice/cage).

The present disclosure features compounds comprising modified peptides of the corticotropin releasing factor (CRF)

family, specifically urocortin or urocortin-related peptides, or derivatives thereof, and conjugates comprising such modified peptides or derivatives covalently attached to a blood component, preferably a serum protein. In a specific embodiment, the urocortin or urocortin-related peptide is selected from the group consisting of urocortin 1, urocortin 2, urocortin 3, SRP, and SCP, and derivatives of any of the foregoing. In certain embodiments, a urocortin or urocortin-related peptide, or a derivative thereof, is a peptide that binds to a corticotropin releasing factor type I or type II receptor ("CRFR1" or "CRFR2") or a member of its family of subtypes. In certain embodiments, a urocortin or urocortin-related peptides, or derivative thereof, is a mammalian peptide, specifically, a mouse, rat, guinea pig, rabbit, dog, cat, horse, cow, pig, or primate peptide, or derivative thereof. Preferably, the peptide is a human peptide, or derivative thereof.

As used herein, a "derivative" of a peptide refers to a compound wherein the amino acid sequence of the compound is the same as that of the peptide except for up to but not more than 10, preferably 9, 8, 7, 6, 5, 4, 3, 2, or 1 amino acid insertions, deletions, and/or substitutions of the amino acid sequence of the peptide, e.g., the urocortin or urocortin-related peptide. Preferably, a derivative binds to the same biological receptor as the peptide and thus displays at least some of the biological activity of the peptide. Derivatives of urocortin or urocortin-related peptides are described in more detail in Section I.

Throughout this application, the various embodiments are described with reference to modified peptides and conjugates for purposes of efficiency of description. However, it will be clear to the skilled worker that these embodiments are equally applicable to the modified derivatives of the peptides and conjugates containing such derivatives (unless the specific context of an embodiment indicates otherwise).

A modified peptide described herein comprises a reactive group covalently attached to the peptide. The reactive group is chosen for its ability to form a stable covalent bond with a serum protein, for example, by reacting with one or more amino groups, hydroxyl groups, or thiol groups on the serum protein. Preferably, a reactive group reacts with only one amino group, hydroxyl group, or thiol group on the serum protein. Preferably, a reactive group reacts with a specific amino group, hydroxyl group, or thiol group on the serum protein. A conjugate comprises a modified peptide, or a modified derivative thereof, which is covalently attached to a serum protein via a reaction of the reactive group with an amino group, hydroxyl group, or thiol group on the serum protein. Thus, a conjugate as described herein comprises a modified peptide, or a modified derivative thereof, in which the reactive group has formed a covalent bond to a serum protein. In a preferred embodiment of the modified peptides or conjugates described herein, the reactive group is a maleimide containing group selected from gamma-maleimidebutyrylamide (GMBA) and maleimido propionic acid (MPA).

As used herein, reference to blood or serum proteins means a protein or peptide that can be found in the blood or serum but for purposes of the invention need not be isolated from the blood or serum. Thus, a blood or serum protein as used herein can be chemically synthesized or recombinantly produced. In a specific embodiment, the serum protein is selected from the group consisting of albumin, transferrin, ferritin, IgM, or IgG.

In another embodiment, the serum protein is a steroid binding protein, a thyroxin binding protein, or alpha-2-macroglobulin. In certain embodiments, the modified peptides described herein are conjugated to cells present in the blood, such a erythrocytes or platelets. In a preferred embodiment, the serum protein is albumin, preferably human albumin, preferably recombinant albumin.

As used herein, "albumin" refers to the most abundant protein in blood plasma having a molecular weight of approximately between 65 and 67 kilodaltons in its monomeric form, depending on the species of origin. The term "albumin" is used interchangeably with "serum albumin" and is not meant to define the source of the albumin which forms a conjugate with the modified peptides. Thus, the term "albumin" as used herein may refer either to albumin purified from a natural source such as blood or serous fluids, or it may refer to chemically synthesized or recombinantly produced albumin.

In various embodiments, albumin variants or derivatives of native albumins can be used for formation of conjugates with the modified peptides. In some embodiments, the albumin is a mammalian albumin, or a variant or derivative thereof. Non-limiting examples of mammalian albumins that can be used include human, bovine, ovine, caprine, rabbit, feline, canine, porcine, primate, or rodent albumin. In a preferred embodiment, the mammalian albumin is human albumin. In one embodiment, the human albumin is purified from blood or serous fluids. In another embodiment, the albumin is recombinant albumin. In a particular embodiment, the albumin is recombinant human albumin (referred to herein as "rHA"). In various embodiments, rHA can be produced in a mammalian or non-mammalian organism. In one embodiment, the rHA is produced in a non-mammalian organism. Examples of non-mammalian organisms that can be used for the production of rHA include, without limitation, yeast, bacteria, plants, fungi, and insects. In one embodiment, the rHA is produced in a whole plant or a whole fungus. In another embodiment, the rHA is produced in cultured plant cells, cultured fungus cells, or cultured insect cells. In another embodiment, the rHA is produced in a non-human mammal or in non-human mammalian cells. Examples of non-human mammals that can be used for the production of rHA include, without limitation, those belonging to one of the following: the family Bovidae, the family Canidae, the family Suidae, the order Rodentia, the order Lagomorpha, and the order Primates (excluding humans). In a particular embodiment, the non-human mammal that is used for the production of rHA is selected from the group consisting of a cow, a dog, a pig, a sheep, a goat, a rat, a mouse, a rabbit, a chimpanzee, and a gorilla. In another embodiment, the non-human mammalian cells used for the production of rHA are, without limitation, bovine, canine, porcine, ovine, caprine, rodent, rabbit, or non-human primate cells. The main advantage of rHA produced in a non-human organism compared with albumin purified from human blood or serous fluids is the absence of human-derived products in the manufacturing process of rHA. The use of such controlled production methods leads to a purer product with less structural heterogeneity. Previous studies have indicated that there is no significant difference between soluble rHA and human albumin purified from blood or serous fluids in terms of their biochemical characteristics, radiolabelling efficiency and biological behavior in vitro and in vivo. See Dodsworth et al., 1996, Biotechnol. Appl. Biochem. 24: 171-176. In a particular embodiment, the albumin is the rHA designated by the trade name RECOMBUMIN® (Novozymes Inc., Davis, Calif.). RECOMBUMIN® is a recombinant human albumin that is produced in vitro using recombinant yeast technology, in which genetically modified yeast (Saccharomyces cerevisiae) secrete soluble rHA which is subsequently harvested, purified and formulated for use as an excipient for the manufacture of biologics or a coating for medical devices.

Reactive groups suitable for covalent attachment to urocortin or urocortin-related peptides and their derivatives are discussed in more detail in Section II. In certain embodiments, more than one reactive group is attached to the peptide. Preferably, a single reactive group is attached to a particular defined amino acid of the peptide. Preferably, only one reactive group is attached to a peptide. In one embodiment, a single reactive group is attached to the peptide at a particular defined amino acid of the peptide. In a specific embodiment, a single maleimide containing group, preferably MPA, is attached to the peptide at a particular defined amino acid of the peptide.

In certain embodiments, the reactive group is bound to the peptide via an intervening molecule, or "linking group." In a preferred embodiment, the linking group is a peptide. In a specific embodiment, the linking group is a peptide having a labile chemical bond which is cleavable by an enzyme or which is cleaved under specific chemical conditions, e.g., acidic conditions. In one embodiment, the modified peptide comprises a reactive group covalently attached to the peptide through one or more linking groups. Preferably, the number of linking groups is between 1 and 10. Where more than one linking group is present, the linking groups may be the same or different linking groups.

Linking groups may comprise one or more alkyl groups such as methyl, ethyl, propyl, butyl, etc. groups, alkoxy groups, alkenyl groups, alkynyl groups or amino group substituted by alkyl groups, cycloalkyl groups, polycyclic groups, aryl groups, polyaryl groups, substituted aryl groups, heterocyclic groups, and substituted heterocyclic groups. Linking groups may also comprise polyethoxy aminoacids such as AEA ((2-amino) ethoxy acetic acid) or AEEA ([2-(2-amino)ethoxy)]ethoxy acetic acid). In one embodiment, the one or more linking groups is selected from the group consisting of AEEA, AEA and OA (8-amino octanoic acid). In certain embodiments, the linking group is a peptide having a labile chemical bond which is cleavable by an enzyme or which is cleaved under acidic conditions.

Preferably, the peptide and serum protein (preferably albumin) of the conjugates are present in the conjugate in a 1:1 molar ratio, or an approximately 1:1 molar ratio. In a preferred embodiment, the peptide and serum protein are present in the conjugate in a 1:1 molar ratio, or an approximately 1:1 molar ratio, and the peptide is attached to the reactive group, optionally through a linking group, at substantially only one site on the peptide and the reactive group is attached to the serum protein at substantially only one site on the serum protein. Preferably, the serum protein is albumin, and the single site of attachment of the reactive group to the albumin is preferably the thiol of cysteine 34 of albumin (e.g., via a maleimide linkage). In a specific embodiment, the reactive group is a single MPA reactive group attached to the peptide, optionally through a linking group, at a single defined amino acid and the MPA is covalently attached to albumin at substantially a single amino acid residue of albumin, preferably cysteine 34. In a preferred embodiment, the albumin is recombinant human albumin. In certain embodiments, the reactive group, preferably MPA, is attached to the peptide through one or more linking groups, preferably AEEA, AEA, or OA. In certain examples of embodiments in which the reactive group, preferably MPA, is attached to the peptide through more than one linking group, each linking group can be independently selected from the group consisting preferably of AEA ((2-amino) ethoxy acetic acid), AEEA ([2-(2-amino)ethoxy)]ethoxy acetic acid), and OA. In one embodiment, the reactive group, preferably MPA, is attached to the peptide via 1, 2, 3, 4, 5, or 6 AEA linking groups which are arranged in tandem. In another embodiment, the reactive group, preferably MPA, is attached to the peptide via 1, 2, 3, 4, 5 or 6 AEEA linking groups which are arranged in tandem. In another embodiment, the reactive group, preferably MPA, is attached to the peptide via 1, 2, 3, 4, 5 or 6 OA linking groups which are arranged in tandem.

The present disclosure also provides methods for covalently attaching a modified peptide to a serum protein, thereby forming a conjugate, e.g., a conjugate described herein. In one embodiment, a modified peptide covalently attached to a serum protein is prepared in vivo by administration of a modified peptide directly to a subject such that the reactive group of the peptide forms a covalent bond with one or more serum proteins in vivo. Such modified peptides for in vivo conjugation with serum proteins are referred to herein as "prodrugs." The prodrug may optionally contain one or more protecting groups which prevent the reactive group from forming covalent bonds in vitro. Preferably, the protecting group of a prodrug according to the invention is labile in vivo, so that the reactive group is released from its protection and is free to covalently bond to a serum protein in vivo after administration to the subject.

In another embodiment, a modified peptide comprising a serum protein is prepared in vitro (ex vivo) by covalently attaching the modified peptide to the serum protein in vitro such that the reactive group of the peptide forms a covalent bond with the serum protein. In one embodiment, the serum protein is autologous to the subject. In a specific embodiment, the serum protein is isolated from the subject. In certain embodiments, the isolated serum protein from the subject is purified from other proteins present in the blood and/or from blood cells before it is covalently attached to the modified peptide. In accordance with this embodiment, the resulting conjugate is administered to the subject from which the serum protein was isolated, or to an autologous subject. In another embodiment, the serum protein is a recombinant serum protein. Preferably, the serum protein is recombinant albumin, most preferably the serum protein is recombinant human albumin.

In a preferred embodiment, a conjugate described herein is formed by contacting a modified peptide comprising a maleimido group with a thiol-containing serum protein, preferably albumin, under conditions comprising a pH of between about 6.5 and 7.4, thereby preferably forming a stable thioether linkage which cannot be cleaved under physiological conditions. In certain preferred embodiments, the serum protein is recombinant human albumin.

In one embodiment, the modified peptide is amidated at its C-terminal end. In another embodiment, the modified peptide is not amidated at its C-terminal end. A conjugate can also comprise such an amidated peptide.

The present disclosure provides conjugates having improved pharmacokinetic properties compared to unconjugated peptides. The pharmacokinetic properties of a peptide include, for example, its rate of absorption and excretion, its tissue distribution profile, its rate of metabolism and its toxicity. Preferably, the conjugates have a decreased rate of excretion and/or an increased circulating half-life in vivo, compared to unconjugated peptides. Pharmacokinetic properties are discussed in more detail in Section III.

The modified peptides and conjugates described herein preferably retain at least some of the biological activity of the corresponding unmodified or unconjugated peptides. In certain embodiments, a modified peptide or conjugate has improved biological activity compared to the corresponding unmodified or unconjugated peptide. Biological activity includes in vitro activity, for example, receptor binding, e.g., to a CRFR1 or CRFR2 or a member of its family of subtypes. CRFR1 and CRFR2 are described, for example, in Liaw wt al. (1996) Endocrinology 137:72-74, Lovenberg et al. (1995) PNAS USA 92:836-840; Perrin et al. (1995) PNAS USA 92:2969-2973; and Perrin et al. (1993) Endocrinology 133: 3058-3061. Biological activity also includes in vivo activity, for example, the ability to modulate arousal, anxiety, cognitive functions, and appetite. In certain embodiments, biological activity includes modulated (e.g., increased) gastric emptying, modulated (e.g., increased) gastric acid secretion, modulated (e.g., decreased) body weight or body mass index, modulated (e.g., decreased) nutrient availability and modulated (e.g., decreased) food intake, and/or improved regulation of glycemic control. Additional biological activities include hypotensive activity, the ability to increase coronary blood flow or left ventricular ejection fraction, increase vasodilation, cardiac intropic effect, and the ability to decrease vascular resistance or renal function. Further biological activities include modulation of muscle mass through increase or hypertrophy or through decreased loss from atrophy or wasting. Biological activity can be measured by any means available in the art such as, e.g., methods described in Hashimoto et al. (2004) Peptides 25:1711-1721 and Takahashi et al. (2004) Peptides 25:1723-1731.

I. Derivatives

In certain embodiments, a modified peptide is a derivative of a urocortin or urocortin-related peptide. In certain embodiments, a conjugate comprises a modified derivative of a urocortin or urocortin-related peptide. A derivative of a urocortin or urocortin-related peptide includes one or more amino acid substitutions, deletions, and/or additions that are not present in the naturally occurring peptide. Preferably, the number of amino acids substituted, deleted, or added is 1, 2, 3, 4, 5, 6, 7, 8, 9, or 10 amino acids.

In one embodiment, such a derivative contains one or more amino acid deletions, substitutions, or additions at the amino and/or carboxy terminal end of the peptide. In another embodiment, such a derivative contains one or more amino acid deletions, substitutions, or additions at any residue within the length of the peptide.

In certain embodiments, the amino acid substitutions may be conservative or non-conservative amino acid substitutions. Conservative amino acid substitutions are made on the basis of similarity in polarity, charge, solubility, hydrophobicity, hydrophilicity, and/or the amphipathic nature of the amino acid residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for another class.

In certain embodiments, an amino acid substitution may be a substitution with a non-classical amino acid or chemical amino acid analog. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In certain embodiments, a derivative of a urocortin or urocortin-related peptide shares an overall sequence homology with urocortin 1, urocortin 2, urocortin 3, SRP, or SCP of at least 75%, at least 85%, at least 95%, at least 98%, or at least 99%. Percent homology in this context means the percentage of amino acid residues in the candidate sequence that are identical (i.e., the amino acid residues at a given position in the alignment are the same residue) or similar (i.e., the amino acid substitution at a given position in the alignment is a conservative substitution, as discussed above), to the corresponding amino acid residue in a urocortin 1, urocortin 2, urocortin 3, SRP, or SCP peptide after aligning the sequences and introducing gaps, if necessary, to achieve the maximum percent sequence homology. In certain embodiments, a derivative of a urocortin or urocortin-related peptide is characterized by its percent sequence identity or percent sequence similarity with a urocortin 1, urocortin 2, urocortin 3, SRP, or SCP peptide. Sequence homology, including percentages of sequence identity and similarity, are determined using sequence alignment techniques well-known in the art, preferably computer algorithms designed for this purpose, using the default parameters of said computer algorithms or the software packages containing them. In certain embodiments, a derivative of a urocortin or urocortin-related peptide shares an overall sequence identity with urocortin 1, urocortin 2, urocortin 3, SRP or SCP of at least 75%, 85%, 95%, 98% or 99%.

Nonlimiting examples of computer algorithms and software packages incorporating such algorithms include the following. The BLAST family of programs exemplify a preferred, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and XBLAST), Altschul et al., 1997, *Nucleic Acids Res.* 25:3389-3402 (describing Gapped BLAST, and PSI-Blast). Another preferred example is the algorithm of Myers and Miller (1988 *CABIOS* 4:11-17) which is incorporated into the ALIGN program (version 2.0) and is available as part of the GCG sequence alignment software package. Also preferred is the FASTA program (Pearson W. R. and Lipman D. J., Proc. Nat. Acad. Sci. USA, 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find best single region of similarity between two sequences, and which is preferable where the two sequences being compared are dissimilar in length; and GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length.

In certain embodiments, a derivative of a urocortin or urocortin-related peptide shares a primary amino acid sequence homology over the entire length of the sequence, without gaps, of at least 55%, at least 65%, at least 75%, or at least 85% with urocortin 1, urocortin 2, urocortin 3, SRP, or SCP. In a preferred embodiment, a modified urocortin peptide shares a primary amino acid sequence homology over the entire length of the sequence, without gaps, of at least 90% or at least 95% with urocortin 1, urocortin 2, urocortin 3, SRP, or SCP.

In a preferred embodiment, the percent identity or similarity is determined by determining the number of identical (for percent identity) or conserved (for percent similarity) amino acids over a region of amino acids, which region is equal to the total length of the shortest of the two peptides being compared (or the total length of both, if the sequence of both are identical in size). In another embodiment, percent identity or similarity is determined using a BLAST algorithm, with default parameters.

II. Reactive Groups

A reactive group is a chemical group which, after conjugation to a urocortin or urocortin-related peptide, is capable of forming a covalent bond with a serum protein. The reactive group is the chemical group that forms the covalent bond with a serum protein to form the conjugates described herein. Thus, in the context of a conjugate, the "reactive group" has already reacted with the serum protein to form a covalent bond with the serum protein.

A reactive group may form a covalent bond with a serum protein, for example, through an amino, hydroxyl, carboxyl, or thiol group of the serum protein. Preferably, a reactive group forms only one covalent bond with the serum protein, most preferably at a specifically defined amino acid of the serum protein. Such reactive groups are covalently attached to a urocortin or urocortin-related peptide of interest to form a modified urocortin or urocortin-related peptide. Reactive groups are preferably stable in an aqueous environment. In specific embodiments, the reactive group comprises a carboxy, phosphoryl, or acyl group. In certain embodiments, the acyl group is an ester or a mixed anhydride, or an imidate. In certain embodiments, the reactive group comprises a phenolic group, a thiol ester, an alkyl ester, or a phosphate ester.

In one embodiment, the reactive group comprises an ester which forms a covalent bond with a hydroxyl group of a serum protein. In one embodiment, the reactive group comprises a maleimide or a maleimido group which forms a covalent bond with a thiol group of a serum protein. In one embodiment, the reactive group comprises a thiol group which forms a covalent bond with an imidate or thioester group of a serum protein. In one embodiment, the reactive group comprises a carboxy, phosphoryl, or acyl group which forms a covalent bond with an amino group of a serum protein.

In one embodiment, the reactive group comprises a succinimidyl or a maleimido group. A succinimide containing reactive group may be referred to herein as a succinimidyl group. A maleimide containing reactive group may be referred to herein as a maleimido group. In a specific embodiment, the reactive group is selected from the group consisting of N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS), GMBA, and MPA.

In one embodiment, the reactive group comprises an NHS ester which forms a covalent bond with the epsilon amine of a lysine residue of a serum protein. Other reactive groups which may be utilized are described in U.S. Pat. No. 5,612,034, which is hereby incorporated by reference.

In a preferred embodiment, the reactive group comprises a maleimide containing group such as GMBA or MPA which forms a covalent bond with a thiol group of a serum protein. In a specific embodiment, the reactive group forms a covalent bond with the thiol group of a cysteine of the serum protein. Preferably, the reactive group forms a covalent bond with cysteine 34 (Cys34) of albumin.

A. Maleimide Containing Reactive Groups

A modified peptide comprising a maleimide containing reactive group offers several advantages over a modified peptide comprising another reactive group, such as NHS or sulfo-NHS. First, in contrast to NHS-peptides, maleimide-peptides are generally stable in aqueous solutions and in the presence of free amines, providing a modified peptide product with a longer shelf-life. Since maleimide containing groups will only react with free thiols, protecting groups are generally not necessary to prevent the maleimide-peptide from reacting with itself or with other peptides in solution. The increased stability of the maleimide-peptide facilitates further purification steps, which may include chromatographic steps such as high pressure liquid chromatography ("HPLC"). The inclusion of further purification steps is preferred for the preparation of highly purified products suitable for in vivo use.

Another advantage of a modified peptide comprising a maleimide reactive group is the preferential reaction of the maleimide with thiol groups on the serum proteins rather than with amino groups, which are favored by NHS reactive groups. This means that a modified peptide comprising a maleimide group will covalently bond to fewer different serum proteins in vivo because thiol groups are less abundant on serum proteins than amino groups. Specifically, a modified peptide of the invention comprising a maleimide group is most likely to form a covalent bond in vivo with either albumin or IgG, because both of these serum proteins contain one or more accessible free thiol groups.

A further advantage of a modified peptide comprising a maleimide reactive group is the ability to form well-defined conjugates with the serum protein, albumin, which is the most abundant serum protein. Since albumin contains only a single free thiol, the thiol of Cys34, the maleimide group of the modified peptide preferentially binds to albumin only at Cys34, giving conjugates of approximately a 1:1 molar ratio of peptide to albumin. Thus, a distinct advantage of the maleimide peptides described herein is the ability to reproducibly form conjugates with albumin in an approximately 1:1 molar ratio with the site of attachment to albumin being a specifically defined amino acid residue on albumin, i.e., Cys 34. Other techniques, such as glutaraldehyde, DCC, EDC and other chemical activations of, for example, free amines, lack this selectivity and give instead heterogeneous populations of conjugates in which the peptide may be covalently bound to the serum protein at any one of a number of possible amino acid residues, e.g., lysine residues, and wherein the serum protein may conjugate to multiple peptides. For example, albumin contains 52 lysine residues, 25-30 of which are located on the surface of the protein and accessible for conjugation. A technique which utilizes chemical activation of amines, or a modified peptide comprising a reactive group which preferentially binds to amines, can form conjugates with albumin at any one of these available lysine residues. The result is multiple conjugation products, some containing 0, 1, 2 or more peptides per albumin, and each having peptides randomly coupled to any one of the 25-30 available lysines residues. Given the numerous combinations possible, characterization of the exact composition and nature of each batch becomes difficult.

In a preferred embodiment, a single reactive group is covalently attached at a defined site of the modified peptide. In a preferred embodiment of the conjugate, a single reactive group is covalently attached at a defined site of the modified peptide and the reactive group is covalently attached to a single defined site of albumin, preferably to the thiol group of amino acid residue Cys34 of albumin. Preferably, the reactive group of a modified peptide or conjugate comprises a maleimide group and forms peptide:albumin conjugates of approximately a 1:1 molar ratio. In certain embodiments, a 1:1 molar ratio of peptide to serum protein is preferred over higher ratios because a 1:1 molar ratio provides better biological activity than higher ratios (see e.g., Stehle et al. 1997 Anti-Cancer Drugs 8:677-685, incorporated herein in its entirety). In one embodiment, the reactive group, e.g., maleimide group, is attached at the N-terminus of the peptide or the C-terminus of the peptide. In one embodiment, the reactive group is attached to at an ϵ-amino a group of a lysine present in the amino acid sequence of the peptide. In one embodiment, one or more lysine present in the amino acid sequence of the peptide is deleted or substituted to a non-lysine amino acid residue within the peptide sequence. In some embodiments, a lysine residue that can be attached with the reactive group, e.g., the maleimide group, is added to the peptide sequence, e.g., inserted or substituting a non-lysine residue in the peptide. In some embodiments, the amino acid sequence of the peptide has been modified so that only one lysine is present in the amino acid sequence of the peptide.

In an embodiment where the modified peptide is administered to a subject, the modified peptide comprising a maleimide group will form a conjugate in vivo with albumin preferentially over other thiol-containing serum proteins. The preferential conjugation to albumin is likely because the free thiol of albumin Cys34 has increased reactivity relative to free thiols of other serum proteins. This is due in part to the low pKa of albumin Cys34, making the ionized form of this cysteine predominant under normal physiological conditions and thereby increasing the reactivity of this residue. Albumin Cys34 is also more reactive due in part to its location in a crevice close to the surface of one loop of region V of albumin, making it very accessible.

In preferred embodiments in which the formation of a conjugate with albumin or an albumin variant or derivative is done ex vivo, albumin, albumin variants or derivatives for use in forming a conjugate described herein may be obtained using methods or materials known to those of skill in the art. For instance, albumin can be obtained from a commercial source, e.g., as RECOMBUMIN® (Novozymes Inc., Davis, Calif.); PLASBUMIN® (Talecris Biotherapeutics, Research Triangle Park, N.C.); ALBAGEN®, (New Century Pharmaceuticals, Huntsville, Ala.); human albumin (Cortex-Biochem, San Leandro, Calif.), human serum albumin, ZLB Behring (King of Prussia, Pa.), or ALBREC® (Mistubishi Pharma, Japan).

B. Peptide Synthesis

The peptides described herein, including peptide linker groups, may be synthesized by standard methods of solid or solution phase peptide chemistry. A summary of the solid phase techniques may be found in Stewart and Young (1963) Solid Phase Peptide Synthesis, W. H. Freeman Co. (San Francisco), and Meienhofer (1973) Hormonal Proteins and Peptides, Academic Press (New York). For classical solution synthesis see Schroder and Lupke, The Peptides, Vol. 1, Academic Press (New York).

In general, these methods comprise the sequential addition of one or more amino acids or suitably protected amino acids to a growing peptide chain. Normally, either the amino or carboxyl group of the first amino acid is protected by a suitable protecting group. The protected amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth. After all the desired amino acids have been linked in the proper sequence, any remaining protecting groups (and any solid support) are removed sequentially or concurrently to afford the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

In certain embodiments, the peptides described herein are synthesized with amino- and carboxy-protecting groups for use as pro-drugs. Protecting groups are chemical moieties which block a reactive group on the peptide to prevent undesirable reactions. In a preferred embodiment, a modified peptide is synthesized with one or more protecting groups that are designed to be cleaved in vivo, thereby exposing the reactive group or groups of the modified peptide to serum proteins after administration of the peptide to a subject. Further examples of protecting groups are provided in the sections that follow.

1. Solid Phase Synthesis

In a preferred embodiment, the peptides described herein are synthesized using solid phase chemistry. For example, as described by Steward and Young, (1984) Solid Phase Peptide Synthesis, $2^{nd}$ ed., Pierce Chemical Co. (Rockford, Ill.). In one embodiment of the method, the N-terminal amino acid is protected by an acid or base sensitive group and the C-terminal amino acid is attached to a suitable solid support or resin. In another embodiment of the method, the C-terminal amino acid is protected by an acid or base sensitive group and the N-terminal amino acid is attached to a suitable solid support or resin.

A suitable protecting group is stable to the conditions of peptide linkage formation while being readily removable without destruction of the growing peptide chain or racemization of any of the chiral centers contained therein. Preferred protecting groups include acetyl, fluorenylmethyloxycarbonyl (FMOC), t-butyloxycarbonyl (BOC), and benzyloxycarbonyl (CBZ). Further examples of suitable protecting groups include biphenylisopropyloxycarbonyl, t-amyloxycarbonyl, isobornyloxycarbonyl, αα-dimethyl-3,5-dimethoxybenzyloxycarbonyl, o-nitrophenylsulfenyl, and 2-cyano-t-butyloxycarbonyl. Additional protecting groups suitable for use in the methods of the invention are found in U.S. Pat. No. 5,493,007 which is hereby incorporated by reference.

The FMOC protecting group is particularly preferred for the synthesis of the peptides. Other preferred protecting groups are selected from among the following: for the protection of the amino side chain groups of lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl are preferred; for the protection of the hydroxyl group of the phenolic ring of tyrosine, benzyl, o-bromobenzyloxycarbonyl, 2,6-dichlorobenzyl, isopropyl, t-butyl (t-Bu), cyclohexyl, cyclopenyl and acetyl (Ac) are preferred; for the protection of the hydroxyl side chain group of serine, t-butyl, benzyl and tetrahydropyranyl are preferred; for protection of the imidazole side chain of histidine, trityl, benzyl, Cbz, p-toluenesulfonyl and 2,4-dinitrophenyl are preferred; for protection of the indole side chain of tryptophan, formyl is preferred; for the protection of the carboxyl side chain of aspartic acid and glutamic acid, benzyl and t-butyl are preferred; and for protection of the thiol group of cysteine, triphenylmethyl (trityl) is preferred.

Suitable solid supports are those materials which are inert to the reagents and reaction conditions of the stepwise condensation-deprotection reactions, as well as being insoluble in the media used. The preferred solid support for synthesis of C-terminal carboxy peptides is 4-hydroxymethylphenoxymethyl-copoly(styrene-1% divinylbenzene). The preferred solid support for-C-terminal amide peptides is the 4-(2',4'-dimethoxyphenyl-Fmoc-aminomethyl)phenoxyacetamidoethyl resin available from Applied Biosystems (Foster City, Calif.). The C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP) or bis (2-oxo-3-oxazolidinyl)phosphine chloride (BOPCl), mediated coupling for from about 1 to about 24 hours at a temperature of between 100 and 50 degrees Celsius in a solvent such as dichloromethane or DMF.

When the solid support is 4-(2',4'-dimethoxyphenyl-Fmoc-aminomethyl)phenoxy-acetamidoethyl resin, the FMOC group is cleaved with a secondary amine, preferably piperidine, prior to coupling with the C-terminal amino acid as described above. The preferred method for coupling to the deprotected 4-(2',4'-dimethoxyphenyl-Fmoc-aminomethyl) phenoxy-acetamidoethyl resin is O-benzotriazol-1-yl-N,N,N',N'-tetramethyluroniumhexafluoro-phosphate (HBTU, 1 equiv.) and 1-hydroxybenzotriazole (HOBT, 1 equiv.) in DMF. The coupling of successive protected amino acids can be carried out in an automatic peptide synthesizer according to manufacturer's instructions and art-recognized procedures. Where the N-terminal amino acids of the growing peptide chain are protected with FMOC, the removal of the FMOC protecting group is accomplished by treatment with a secondary amine, preferably piperidine. Each protected amino acid is then introduced in about 3-fold molar excess, and the coupling is preferably carried out in DMF. The coupling agent is normally O-benzotriazol-1-yl-N,N,N',N'-tetramethyluroniumhexafluorophosphate (HBTU, 1 equiv.) and 1-hydroxybenzotriazole (HOBT, 1 equiv.).

At the end of the solid phase synthesis, the peptide is removed from the resin and deprotected, either in successive steps or in a single step. Removal of the peptide and deprotection can be accomplished in a single step by treating the resin-bound peptide with a cleavage reagent comprising thianisole, water, ethanedithiol and trifluoroacetic acid. In cases wherein the C-terminal end of the peptide is an alkylamide, the resin is cleaved by aminolysis with an alkylamine. Alternatively, the peptide may be removed by transesterification, e.g., with methanol, followed by aminolysis or by direct transamidation. The protected peptide may be purified at this point or taken to the next step directly. The removal of the side chain protecting groups is accomplished using the cleavage cocktail described above.

The fully deprotected peptide is purified by a sequence of chromatographic steps employing any or all of the following: ion exchange on a weakly basic resin (acetate form); hydrophobic adsorption chromatography on underivatized polystyrene-divinylbenzene (for example, Amberlite XAD); silica gel adsorption chromatography; ion exchange chromatography on carboxymethylcellulose; partition chromatography, e.g., on Sephadex G-25, LH-20 or countercurrent distribution; high performance liquid chromatography (HPLC), especially reverse-phase HPLC on octyl- or octadecylsilyl-silica bonded phase column packing.

Molecular weights of the synthesized peptides are determined, for example, using Fast Atom Bombardment (FAB) Mass Spectroscopy.

2. Amino-Protecting Groups

The term "amino-protecting group" refers to those groups intended to protect the amino-terminal end of an amino acid or peptide or to protect the amino group of an amino acid or peptide against undesirable reactions. Commonly used amino-protecting groups are disclosed in Greene (1981) Protective Groups In Organic Synthesis (John Wiley & Sons, New York), which is hereby incorporated by reference. Additionally, protecting groups can be used which are readily cleaved in vivo, for example, by enzymatic hydrolysis, thereby exposing the amino group for reaction with serum proteins in vivo.

Amino-protecting groups comprise lower alkanoyl groups such as formyl, acetyl ("Ac"), propionyl, pivaloyl, and t-butylacetyl; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, and 4-nitrobenzoyl; sulfonyl groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, $\alpha\alpha$-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2, -trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, and phenylthiocarbonyl; arylalkyl groups such as benzyl, triphenylmethyl, benzyloxymethyl, 9-fluorenylmethyloxycarbonyl (Fmoc) and silyl groups such as trimethylsilyl.

3. Carboxy Protecting Groups

The term "carboxy protecting group" refers to a carboxylic acid protecting ester or amide group employed to block or protect the carboxylic acid functionality. Carboxy protecting groups are disclosed in Greene, "Protective Groups in Organic Synthesis" pp. 152-186 (1981), which is hereby incorporated by reference. Additionally, a carboxy protecting group can be used as a pro-drug whereby the carboxy protecting group can be readily cleaved in vivo, for example by enzymatic hydrolysis, thereby exposing the carboxy group for reaction with serum proteins in vivo. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated by reference.

Representative carboxy protecting groups are $C_1$-$C_8$ lower alkyl (e.g., methyl, ethyl or t-butyl); arylalkyl such as phenethyl or benzyl and substituted derivatives thereof such as alkoxybenzyl or nitrobenzyl groups; arylalkenyl such as phenylethenyl; aryl and substituted derivatives thereof such as 5-indanyl; dialkylaminoalkyl such as dimethylaminoethyl); alkanoyloxyalkyl groups such as acetoxymethyl, butyryloxymethyl, valeryloxymethyl, isobutyryloxymethyl, isovaleryloxym ethyl, 1-(propionyloxy)-1-ethyl, 1-(pivaloyloxyl)-1-ethyl, 1-methyl-1-(propionyloxy)-1-ethyl, pivaloyloxymethyl, and propionyloxymethyl; cycloalkanoyloxyalkyl groups such as cyclopropylcarbonyloxymethyl, cyclobutylcarbonyloxymethyl, cyclopentylcarbonyloxymethyl, and cyclohexylcarbonyloxymethyl; aroyloxyalkyls such as benzoyloxymethyl and benzoyloxyethyl; arylalkylcarbonyloxyalkyls such as benzylcarbonyloxymethyl and 2-benzylcarbonyloxyethyl; alkoxycarbonylalkyl or cycloalkyloxycarbonylalkyl such as methoxycarbonylmethyl, cyclohexyloxycarbonylmethyl, and 1-methoxycarbonyl-1-ethyl; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, and 1-cyclohexyloxycarbonyloxy-1-ethyl; aryloxycarbonyloxyalkyl such as 2-(phenoxycarbonyloxy)ethyl, and 2-(5-indanyloxycarbonyloxy)ethyl; alkoxyalkylcarbonyloxyalkyl such as 2-(1-methoxy-2-methylpropan-2-oyloxy)ethyl; arylalkyloxycarbonyloxyalkyl such as 2-(benzyloxycarbonyloxy)ethyl; arylalkenyloxycarbonyloxyalkyl such as 2-(3-phenylpropen-2-yloxycarbonyloxy)ethyl; alkoxycarbonylaminoalkyl such as t-butyloxycarbonylaminomethyl; alkylaminocarbonylaminoalkyl such as methylaminocarbonylaminomethyl; alkanoylaminoalkyl such as acetylaminomethyl; heterocycliccarbonyloxyalkyl such as 4-methylpiperazinylcarbonyloxymethyl; dialkylaminocarbonylalkyl such as dimethylaminocarbonylmethyl, diethylaminocarbonylmethyl; (5-(loweralkyl)-2-oxo-1,3-dioxolen4-yl)alkyl such as (5-t-butyl-2-oxo-1,3-dioxolen-4-yl)methyl; and (5-phenyl-2-oxo-1,3-dioxolen-4-yl)alkyl such as (5-phenyl-2-oxo-1,3-dioxolen-4-yl)methyl.

Preferred carboxy-protected peptides are peptides wherein the protected carboxy group is a lower alkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, and phenylethyl ester or an alkanoyloxyalkyl, cycloalkanoyloxyalkyl, aroyloxyalkyl or an arylalkylcarbonyloxyalkyl ester. Preferred amide carboxy protecting groups are lower alkylaminocarbonyl groups. For example, aspartic acid may be protected at the α-C-terminal by an acid labile group (e.g., t-butyl) and protected at the β-C-terminal by a hydrogenation labile group (e.g., benzyl) then deprotected selectively during synthesis.

III. Pharmacokinetic Properties

The compounds, modified peptides, modified derivatives, and/or conjugates described herein preferably exhibit improved pharmacokinetic properties compared to unmodified or unconjugated peptides. For example, the peptides described herein preferably exhibit improved profiles of one or more of the following properties: absorption, distribution, metabolism, excretion and toxicity. These properties are determined using standard pharmacological and profiling assays available in the art. Preferably, a compound (comprising a modified peptide or derivative with a reactive group as described herein) or conjugate for therapeutic use has one or more of the following characteristics: a slower rate of elimination compared to the corresponding unmodified or unconjugated peptide, an increased circulating half-life compared to the corresponding unmodified or unconjugated peptide, and solubility in aqueous solution. Preferably, a compound or conjugate for therapeutic use has increased bioavailability upon administration compared to the unmodified or unconjugated peptide.

In certain preferred embodiments, the compounds and conjugates described herein for therapeutic use persist in the serum following administration for longer than the corresponding unmodified or unconjugated peptide. Methods for determining persistence after administration are well known in the art. For example, antibodies that bind to the peptide can be used to determine persistence (and if necessary remove the compound or conjugate) by methods described in PCT Publication No.: WO 00/69900. A typical experimental design includes assessing exposure at 15 min, 1 hr, 3 hr, 6 hr, 24 hr, and 48 hr after administration at an appropriate dose, e.g., 10 mg/kg in a mammal such as a mouse, guinea pig, or dog. Peptide levels in the serum can be measured using standard techniques, such as LC/MS/MS technology.

The conjugates described herein can also demonstrate an altered, e.g., decreased, toxicology profile as compared to the unconjugated peptide. In some embodiments, the toxicology profile is altered by separating the action of the peptide from both central nervous system receptors and peripheral nervous system receptors to, e.g., a preference for peripheral central nervous system receptors. In one embodiment, the conjugates described herein minimize side effects such as nausea and vomiting as compared to the unconjugated peptide. For example, the conjugates described herein can prevent, reduce or eliminate a nausea side effect. Nausea side effects are any unpleasant sensation in the epigastrium, in the back of the throat, or in the abdomen. In some embodiments, nausea may culminate in vomiting. In some embodiments, nausea may not culminate in vomiting. In some embodiments, nausea can be sickness at the stomach, especially when accompanied by a loathing for food and an involuntary impulse to vomit. In some embodiments, nausea can be a feeling of sickness or discomfort in the stomach marked by an urge to vomit.

IV. Therapeutic Uses

The compounds, modified peptides, modified derivatives, and/or conjugates described herein can be used in the prevention or treatment of a disease or disorder in a subject, e.g., a disease or disorder associated with the expression of CRFR1 and/or CRFR2 receptor. Examples of tissues and organs where CRFR1 and CRFR2 are expressed are described, for example, in Hashimoto et al. (2004) Peptides 25:1711-1721 and Takahashi et al. (2004) Peptides 25:1723-1731. Preferably, the disease or disorder is one for which administration of a CRF family peptide, e.g., a urocortin or urocortin-related peptide, to a subject has shown some efficacy. In a preferred embodiment, the disease or disorder is a cardiovascular disease or disorder. In a specific embodiment, the cardiovascular disease or disorder is acute decompensated heart failure (ADHF) or congestive heart failure (CHF). In another embodiment, a compound (comprising a modified peptide or derivative with a reactive group as described above) or conjugate is administered for cardiovascular protection to a subject in need of such cardiovascular protection, for example, a subject who has had a myocardial ischemia/infarction (MI) or has undergone a cardiovascular surgery.

In a specific embodiment, the compounds or conjugates can be used in the prevention or treatment of cardiovascular related diseases or disorders, preferably CHF or ADHF. In another specific embodiment, the compounds or conjugates of the invention can be used for cardiovascular protection, for example, in a subject who has had a MI or has undergone a cardiovascular surgery. In a preferred embodiment, the modified peptide or derivative used in the treatment or prevention of a cardiovascular related disease or disorder is a modified urocortin 1, urocortin 2, urocortin 3, SRP, or SCP peptide or a modified derivative thereof. In another preferred embodiment, a conjugate used in the treatment or prevention of a cardiovascular related disease or disorder comprises a modified urocortin 1, urocortin 2, urocortin 3, SRP, or SCP peptide or a modified derivative thereof.

Nonlimiting examples of diseases and disorders that can be prevented or treated by administration of one or more of the compounds or conjugates of the invention include, but are not limited to, stress; anxiety; memory or learning dysfunction; appetite dysfunction such as related to obesity or cachexia; modulation of arousal; modulation of skeletal muscle mass; modulation of energy balance; modulation of fluid homeostasis; modulation of gastric motor function; modulation of reproductive functions such as maintenance of ovarian and placental function, pregnancy, and labor; modulation of the immune response; modulation of inflammatory response; physiologic disorders such as abnormal body temperature, abnormal levels of corticotropin releasing factor (CRF), abnormal levels of adreno corticotropic hormone (ACTH), and modulation of caloric intake.

In some embodiments, a disease or disorder that can be alleviated by reducing caloric or nutrient intake means any disease or disorder in a subject that is either caused by, complicated by or aggravated by a relatively high nutrient availability, or that can be alleviated by reducing nutrient availability, for example, decreasing food intake. Such conditions and disorders include, but are not limited to, obesity, diabetes, including type 2 diabetes, eating disorders and insulin-resistance syndromes (e.g., Syndrome X).

In some aspects, the compounds or conjugates can be used to treat obesity in an obese or overweight subject. While "obesity" is generally defined as a body mass index over 30, for purposes of this disclosure, any subject including those with a body mass index of less than 30, who needs or wished to reduce body weight is included in the scope of "obese". In some aspects, the compounds or conjugates can decrease a body mass index while not necessarily decreasing body weight. For example, administration of a compound or conjugate described herein can result in increase muscle mass such that the subject may exhibit a decrease in body mass index without a decrease in body weight.

In other aspects, the compounds or conjugates are used to decrease body weight, appetite and/or food intake in a subject. In some embodiments, the compounds or conjugates can increase muscle mass in the subject. The subject can be of average weight, be overweight or be obese.

Compounds and conjugates described herein can also be used to increase gastric emptying and/or regulation of glycemic control in a subject by administering the compound or conjugate to the subject.

In other aspects, the compounds or conjugates can be used to treat or prevent a disorder associated with muscular atrophy, the ability to modulate muscle mass through increase or hypertrophy or through decrease loss from atrophy and wasting. Examples of such disorders include Duschenne muscular dystrophy and Becker muscular dystrophy.

V. Compositions and Methods of Administering

The disclosure also provides compositions (including pharmaceutical compositions) comprising a compound or conjugate described herein, and one or more of pharmaceutically acceptable carrier, excipient, and diluent. In certain embodiments, a composition of the invention may also contain minor amounts of wetting or emulsifying agents, or pH buffering agents. In a specific embodiment, the pharmaceutical composition is pharmaceutically acceptable for administration to a human. In certain embodiments, the pharmaceutical composition comprises a therapeutically or prophylactically effective amount of a compound or conjugate described herein. The amount of a compound or conjugate of the invention that will be therapeutically or prophylactically effective can be determined by standard clinical techniques. Exemplary effective amounts are described in more detail in Section V.C. In certain embodiments, a composition of the invention may also contain a stabilizer. A stabilizer is a compound that reduces the rate of chemical degradation of the modified peptide of the composition. Suitable stabilizers include, but are not limited to, antioxidants, such as ascorbic acid, pH buffers, or salt buffers.

The pharmaceutical compositions can be in any form suitable for administration to a subject, preferably a human subject. In certain embodiments, the compositions are in the form of solutions, suspensions, emulsion, tablets, pills, capsules, powders, and sustained-release formulations. The compositions may also be in particular unit dosage forms. Examples of unit dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

In a specific embodiment, the subject is a mammal such as a cow, horse, sheep, pig, fowl, cat, dog, mouse, rat, rabbit, or guinea pig. In a preferred embodiment, the subject is a human. Preferably, the pharmaceutical composition is suitable for veterinary and/or human administration. In accordance with this embodiment, the term "pharmaceutically acceptable" means approved by a regulatory agency of the Federal or a state government or listed in the U.S. Pharmacopeia or other generally recognized pharmacopeia for use in animals, and more particularly for use in humans.

Suitable pharmaceutical carriers for use in the compositions are sterile liquids, such as water and oils, including those of petroleum, animal, vegetable or synthetic origin. In a specific embodiment, the oil is peanut oil, soybean oil, mineral oil, or sesame oil. Water is a preferred carrier when the pharmaceutical composition is administered intravenously. Saline solutions and aqueous dextrose and glycerol solutions can also be employed as liquid carriers, particularly for injectable solutions. Further examples of suitable pharmaceutical carriers are known in the art, e.g., as described by E. W. Martin in *Remington's Pharmaceutical Sciences* (1990) 18th ed. (Mack Publishing, Easton Pa.).

Suitable excipients for use in the compositions include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. Whether a particular excipient is suitable for incorporation into a pharmaceutical composition depends on a variety of factors well known in the art including, but not limited to, the route of administration and the specific active ingredients in the composition.

In certain embodiments, a composition of the invention is an anhydrous composition. Anhydrous compositions can be prepared using anhydrous or low moisture containing ingredients and low moisture or low humidity conditions. Compositions comprising modified peptides having a primary or secondary amine are preferably anhydrous if substantial contact with moisture and/or humidity during manufacturing, packaging, and/or storage is expected. An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

A. Formulations

Pharmaceutical compositions comprising the compounds or conjugates described herein, or their pharmaceutically acceptable salts and solvates, are formulated to be compatible with the intended route of administration. The formulations are preferably for subcutaneous administration, but can be for administration by other means such as by inhalation or insufflation (either through the mouth or the nose), intradermal, oral, buccal, parenteral, vaginal, or rectal. Preferably, the compositions are also formulated to provide increased chemical stability of the compound during storage and transportation. The formulations may be lyophilized or liquid formulations.

In one embodiment, the compounds or conjugates are formulated for oral administration. Oral formulations can include standard carriers such as pharmaceutical grades of mannitol, lactose, starch, magnesium stearate, sodium saccharine, cellulose, magnesium carbonate, etc. In another embodiment, the compounds or conjugates are formulated for injection. In a preferred embodiment, the compounds or conjugates are sterile lyophilized formulations, substantially free of contaminating cellular material, chemicals, virus, or toxins. In a particular embodiment, the compounds or conjugates are formulated in liquid form. In another particular embodiment, formulations for injection are provided in sterile single dosage containers. In a particular embodiment, formulations for injection are provided in sterile single dosage containers. The formulations may or may not contain an added preservative. Liquid formulations may take such forms as suspensions, solutions or emulsions in oily or aqueous vehicles, and may contain formulation agents such as suspending, stabilizing and/or dispersing agents.

B. Methods of Administration

A compound or conjugate described herein, or a pharmaceutically acceptable salt thereof, is preferably administered as a component of a composition that optionally comprises a pharmaceutically acceptable vehicle. The compound or conjugate is preferably administered subcutaneously. Another preferred method of administration is via intravenous injection of the compound or conjugate.

In certain embodiments, the compound or conjugate is administered by any other convenient route, for example, by infusion or bolus injection, or by absorption through epithelial or mucocutaneous linings (e.g., oral mucosa, rectal, and intestinal mucosa). Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In most instances, administration will result in the release of the compound or conjugate into the bloodstream.

In one embodiment, a compound comprising a maleimide containing reactive group is administered to a subject in a controlled manner such that 80-90% of the administered peptide forms conjugates with albumin and less than 5% forms conjugates with IgG. Such specific conjugation is preferred for in vivo use as it permits an accurate calculation of the estimated half-life of the administered peptide or derivative.

In another embodiment, a compound comprising a maleimide containing reactive group is added to blood, serum, or a saline solution containing serum albumin and/or IgG, under conditions permitting the formation of a covalent bond between the reactive group of the peptide and the albumin and/or IgG, resulting in the formation of a conjugate of the peptide with the albumin or IgG. In a further embodiment, the blood, serum, or saline solution containing the conjugate is administered to a subject.

In certain embodiments, the compounds or conjugates are administered in combination with one or more other biologically active agents as part of a treatment regimen. In certain embodiments, the compounds or conjugates are administered prior to, concurrently with, or subsequent to the administration of the one or more other biologically active agents. In one embodiment, the one or more other biologically active agents is administered in the same pharmaceutical composition with a compound or conjugate described herein. In another embodiment, the one or more other biologically active agents is administered in a separate pharmaceutical composition with a compound or conjugate described herein. In accordance with this embodiment, the one or more other biologically active agents may be administered to the subject by the same or different routes of administration as those used to administer the compound or conjugate.

In one embodiment, the compound or conjugate can be administered with one or more other compounds and compositions that exhibit a long term or short-term action to reduce nutrient availability, including, but not limited to other compounds and compositions that comprise an amylin or amylin agonist, a cholecystokinin (CCK) or CCK agonist, a leptin (OB protein) or leptin agonist, an exendin or exendin agonist, or a GLP-1 or GLP-1 agonist. Suitable amylin agonists include, for example, [25,28,29Pro-]-human amylin (also known as "pramlintide," and described in U.S. Pat. Nos. 5,686,511 and 5,998,367) and salmon calcitonin. The CCK used is preferably CCK octopeptide (CCK-8). Leptin is discussed in, for example, (Pelleymounter, Cullen et al. Science 269: 540-543, 1995) (Halaas, Gajiwala et al. Science 269: 543-6, 1995) and (Campfield, Smith et al. Science 269: 546-549, 1995). Suitable exendins include exendin-3 and exendin-4, and exendin agonist compounds include, for example, those described in PCT Publications WO 99/07404, WO 99/25727, and WO 99/25728.

In another embodiment, the compound or conjugate can be administered with one or more other compound or composition for reducing risk or treating a cardiovascular disease. Compounds or compositions the reduce the risk or treat cardiovascular disease include, but are not limited to, anti-inflammatory agents, anti-thrombotic agents, anti-platelet agents, fibrinolytic agents, thrombolytics, lipid reducing agents, direct thrombin inhibitors, anti-Xa inhibitors, anti-IIa inhibitors, glycoprotein IIb/IIIa receptor inhibitors and direct thrombin inhibitors. Examples of agents that can be administered in combination with the compound or conjugates described herein include bivalirudin, hirudin, hirugen, Angiomax, agatroban, PPACK, thrombin aptamers, aspirin, GPIIb/IIIa inhibitors (e.g., Integrelin), P2Y12 inhibitors, thienopyridine, ticlopidine, and clopidogrel.

C. Dosages and Frequency

The amount of a compound or conjugate described herein, or the amount of a composition comprising the compound or conjugate, that will be effective in the prevention or treatment of a disease or disorder can be determined by standard clinical techniques. In vitro or in vivo assays may optionally be employed to help identify optimal dosage ranges. The precise dose to be employed will also depend, e.g., on the route of administration, the type of invention, and the seriousness of the disease or disorder, and should be decided according to the judgment of the practitioner and each patient's circumstances.

Exemplary doses of the compounds or conjugates described herein, or of compositions (preferably pharmaceutical compositions) comprising same, include milligram or microgram or picogram amounts per kilogram of the subject (e.g., about 10 picogram per kilogram to about 500 milligrams per kilogram, about 100 picograms per kilogram to about 5 milligrams per kilogram, or about 1 microgram per kilogram to about 50 micrograms per kilogram). In specific embodiments, a daily dose is at least 1 µg, 5 µg, 10 µg, 100 µg, 250 µg, 500 µg, 750 µg, 1 mg, 5 mg, 5 mg, 10 mg, 25 mg, 50 mg, 75 mg, or at least 100 mg.

In one embodiment, the dosage is a concentration of 0.0001 to 5000 mM, 0.01 to 500 mM, 0.1 to 300 mM and 1 mM to 100 mM. In another embodiment, the dosage is a concentration of at least 0.1 µM, 1 µM, 5 µM, at least 10 µM, at least 50 µM, at least 100 µM, at least 500 µM, at least 1 mM, at least 5 mM, at least 10 mM, at least 50 mM, at least 100 mM, or at least 500 mM.

In a specific embodiment, the dosage is 0.01 µg/kg or more, preferably 0.1 µg/kg or more, 0.25 µg/kg or more, 0.5 µg/kg or more, 1 µg/kg or more, 2 µg/kg or more, 3 µg/kg or more, 4 µg/kg or more, 5 µg/kg or more, 6 µg/kg or more, 7 µg/kg or more, 8 µg/kg or more, 9 µg/kg or more, or 10 µg/kg or more, 25 µg/kg or more, preferably 50 µg/kg or more, 100 µg/kg or more, 250 µg/kg or more, 500 µg/kg or more, 1 mg/kg or more, 5 mg/kg or more, 6 mg/kg or more, 7 mg/kg or more, 8 mg/kg or more, 9 mg/kg or more, or 10 mg/kg or more of a patient's body weight.

In another embodiment, the dosage is a unit dose of 0.1 µg, 1 µg, preferably 5 µg, 10 µg, 50 µg, 100 µg, 250 µg, 500 µg, 750 µg, 1 mg, 5 mg, 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more.

In another embodiment, the dosage is a unit dose that ranges from about 0.1 µg to about 1 g, preferably about 1 µg to about 500 mg, about 100 µg to about 300 mg, about 1 mg to about 100 mg, 1 mg to about 500 mg, about 10 mg to about 800 mg, about 500 mg to about 1000 mg, or about 5 mg to about 1000 mg.

In certain embodiments, suitable dosage ranges for oral administration are about 0.001 milligram to about 5 grams of a compound or conjugate, or a pharmaceutically acceptable salt thereof, per kilogram body weight per day. In specific embodiments of the invention, the oral dose is about 0.01 milligram to about 100 milligrams per kilogram body weight per day, preferably about 0.1 milligram to about 75 milligrams per kilogram body weight per day, and more preferably about 0.5 milligram to 5 milligrams per kilogram body weight per day. The dosage amounts described herein refer to total amounts administered; that is, if more than one compound or conjugate is administered, then, in some embodiments, the dosages correspond to the total amount administered. In a specific embodiment, oral compositions contain about 10% to about 95% a peptide of the invention by weight.

In some embodiments, suitable dosage ranges for intravenous (i.v.) administration are about 1 picogram to about 100 milligrams per kilogram body weight per day, about 1 microgram to about 10 milligrams per kilogram body weight per day, and about 10 microgram to about 1 milligram per kilogram body weight per day. In some embodiments, suitable dosage ranges for intranasal administration are about 0.01 pg/kg body weight per day to about 1 mg/kg body weight per day. Suppositories generally contain about 0.01 microgram to about 50 milligrams of a compound of the invention per kilogram body weight per day and comprise active ingredient in the range of about 0.1% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration are in the range of about 0.001 milligram to about 50 milligrams, depending on the area of administration. Effective doses may be extrapolated from dose-response curves derived from in vitro or animal model test systems. Such animal models and systems are well known in the art.

In another embodiment, a subject is administered one or more doses of a prophylactically or therapeutically effective amount of a compound or conjugate described herein, or of a composition comprising same, wherein the prophylactically or therapeutically effective amount is not the same for each dose. In another embodiment, a subject is administered one or more doses of a prophylactically or therapeutically effective amount of a compound or conjugate described herein, or of a composition comprising same, wherein the dose of a prophylactically or therapeutically effective amount administered to said subject is increased by, e.g., 0.001 µg/kg, 0.002 µg/kg, 0.005 µg/kg, 0.01 µg/kg, 0.02 µg/kg, 0.04 µg/kg, 0.05 µg/kg, 0.06 iag/kg, 0.08 µg/kg, 0.1 ag/kg, 0.2 µg/kg, 0.25/g/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses. In another embodiment, a subject is administered one or more doses of a prophylactically or therapeutically effective amount of a compound or conjugate described herein, wherein the dose is decreased by, e.g., 0.001 µg/kg, 0.002 µg/kg, 0.005 µg/kg, 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses.

When the compound or conjugate is administered more than once, the administration can occur, for example, at least once a day, once every other day, every two days, every three days, every four day, every five days, every six days, once a week, every 8 days, every nine days or every ten days.

The above-described administration schedules are provided for illustrative purposes only and should not be considered limiting. A person of ordinary skill in the art will readily understand that all doses are within the scope of the invention.

D. Packs/Kits

The disclosure provides a pharmaceutical pack or kit comprising one or more containers filled with one or more of the compounds or conjugates described herein for the prevention or treatment of a disease or disorder, or one or more symptoms thereof.

In one embodiment, the kit comprises a compound or conjugate described herein, in one or more containers. In one embodiment, the kit comprises a pharmaceutical composition described herein, in one or more containers. In one embodiment, the kit optionally contains one or more other biologically active agents useful for the prevention or treatment of a disease or disorder, or one or more symptoms thereof, in one or more other containers. In one embodiment, the kit comprises a compound or conjugate described herein in lyophilized form. In accordance with this embodiment, the kit may optionally contain a container of sterile solution suitable for reconstituting the lyophilized compound or conjugate. In one embodiment, the kit comprises a unit dosage form of a compound or conjugate in one or more containers.

Preferably, a kit further comprises instructions for preventing or treating the disease or disorder, as well as side effects and dosage information for specific methods of administration. Optionally associated with such container(s) can be a notice in the form prescribed by a governmental agency regulating the manufacture, use or sale of pharmaceuticals or biological products, which notice reflects approval by the agency of manufacture, use or sale for human administration.

The following invention is further illustrated by the following examples, which should not be construed as further limiting. The contents of all references, pending patent applications and published patents, cited throughout this application are hereby expressly incorporated by reference.

EXAMPLES

Examples 1-6 provide specific modified urocortin and urocortin-related peptides of the invention, which are amidated at the C-termini. Alternatively, the modified urocortin and urocortin-related peptides may be acids at the C-termini. The term "anchor" as used in the tables below refers to a reactive group, e.g., as described herein, particularly as described in Section II. The reactive group is preferably maleimido propionic acid (MPA). The modified peptides may optionally contain a linking group. The linking group, if present, is preferably selected from the group consisting of AEEA, AEA and OA. Preferably the number of linking groups is between 1 and 6. Where there is more than one linking group, the linking groups can be identical or different linking groups.

These peptides can be covalently attached to a serum protein such as albumin in vivo, following administration to a subject, or in vitro (ex vivo), where the conjugate is to be administered to the subject. Preferably, the peptides are covalently attached to a serum protein, preferably albumin, in vitro, to form a conjugate of the invention.

Amino acids depicted in bold and larger font in the sequences of the tables below indicate an amino acid substitution or addition with reference to the urocortin or urocortin-related peptide sequence depicted at the top of each table.

Example 1

Human Urocortin 1 (40 Amino-acids)

(SEQ ID NO: 1)
DNPSL SIDLT FHLLR TLLEL ARTQS QRERA EQNRI IFDSV-NH2

TABLE 1

Modified peptides of human urocortin 1

| | |
|---|---|
| (anchor-linker)DNPSL SIDLT FHLLR TLLEL ARTQS QRERA EQNRI IFDSV-NH$_2$ | SEQ ID NO: 2 |
| DNPSL SIDLT FHLLK-(ε-linker-anchor) TLLEL ARTQS QRERA EQNRI IFDSV-NH$_2$ | SEQ ID NO: 3 |
| DNPSL SIDLT FHLLR TLLEL AK-(ε-linker-anchor)TQS QRERA EQNRI IFDSV-NH$_2$ | SEQ ID NO: 4 |
| DNPSL SIDLT FHLLR TLLEL ARTQS QK-(ε-linker-anchor)ERA EQNRI IFDSV-NH$_2$ | SEQ ID NO: 5 |

TABLE 1-continued

Modified peptides of human urocortin 1

| | |
|---|---|
| DNPSL SIDLT FHLLR TLLEL ARTQS QREK-(ε-linker-anchor)A EQNRI IFDSV-NH$_2$ | SEQ ID NO: 6 |
| DNPSL SIDLT FHLLR TLLEL ARTQS QRERA EQNK-(ε-linker-anchor)I IFDSV-NH$_2$ | SEQ ID NO: 7 |
| DNPSL SIDLT FHLLR TLLEL ARTQS QRERA EQNRI IFDSVK-(ε-linker-anchor)-NH$_2$ | SEQ ID NO: 8 |

Example 2

Human Urocortin 2 (38 Amino-acids)

(SEQ ID NO: 76)
IVLSL DVPIG LLQIL LEQAR ARAAR EQATT NARIL ARV-NH2

TABLE 2

Modified peptides of human urocortin 2

| | |
|---|---|
| (anchor-linker)IVLSL DVPIG LLQIL LEQAR ARAAR EQATT NARIL ARV-NH2 | SEQ ID NO: 9 |
| IVLSL DVPIG LLQIL LEQAK-(ε-linker-anchor) ARAAR EQATT NARIL ARV-NH2 | SEQ ID NO: 10 |
| IVLSL DVPIG LLQIL LEQAR AK-(ε-linker-anchor)AAR EQATT NARIL ARV-NH2 | SEQ ID NO: 11 |
| IVLSL DVPIG LLQIL LEQAR ARAAK-(ε-linker-anchor) EQATT NARIL ARV-NH2 | SEQ ID NO: 12 |
| IVLSL DVPIG LLQIL LEQAR ARAAR EQATT NAK-(ε-linker-anchor)IL ARV-NH2 | SEQ ID NO: 13 |
| IVLSL DVPIG LLQIL LEQAR ARAAR EQATT NARIL AK-(ε-linker-anchor)V-NH2 | SEQ ID NO: 14 |
| IVLSL DVPIG LLQIL LEQAR ARAAR EQATT NARIL ARVK-(ε-linker-anchor)-NH2 | SEQ ID NO: 15 |
| IVLSL DVPIG LLQIL LEQAR ARAAR EQATT NARIL ARVGH C-NH2 | SEQ ID NO: 92 |

Example 3

Human Urocortin 3 (38 Amino-acids)

(SEQ ID NO: 77)
FTLSL DVPTN IMNLL FNIAK AKNLR AQAAA NAHLM AQI-NH2

TABLE 3

Modified peptides of human urocortin 3

| | |
|---|---|
| (anchor-linker)FTLSL DVPTN IMNLL FNIAK AKNLR AQAAA NAHLM AQI-NH$_2$ | SEQ ID NO: 16 |
| (anchor-linker)FTLSL DVPTN IMNLL FNIAR AKNLR AQAAA NAHLM AQI-NH$_2$ | SEQ ID NO: 17 |
| (anchor-linker)FTLSL DVPTN IMNLL FNIAK ARNLR AQAAA NAHLM AQI-NH$_2$ | SEQ ID NO: 18 |

TABLE 3-continued

Modified peptides of human urocortin 3

| | |
|---|---|
| (anchor-linker)FTLSL DVPTN IMNLL FNIAR ARNLR AQAAA NAHLM AQI-NH₂ | SEQ ID NO: 19 |
| FTLSL DVPTN IMNLL FNIAK-(ε-linker-anchor) AKNLR AQAAA NAHLM AQI-NH₂ | SEQ ID NO: 20 |
| FTLSL DVPTN IMNLL FNIAK(ε-linker-anchor) ARNLR AQAAA NAHLM AQI-NH₂ | SEQ ID NO: 21 |
| FTLSL DVPTN IMNLL FNIAK AK-(ε-linker-anchor)NLR AQAAA NAHLM AQI-NH₂ | SEQ ID NO: 22 |
| FTLSL DVPTN IMNLL FNIAR AK-(ε-linker-anchor)NLR AQAAA NAHLM AQI-NH₂ | SEQ ID NO: 23 |
| FTLSL DVPTN IMNLL FNIAK AKNLK-(ε-linker-anchor) AQAAA NAHLM AQI-NH₂ | SEQ ID NO: 24 |
| FTLSL DVPTN IMNLL FNIAR AKNLK-(ε-linker-anchor) AQAAA NAHLM AQI-NH₂ | SEQ ID NO: 25 |
| FTLSL DVPTN IMNLL FNIAK ARNLK-(ε-linker-anchor) AQAAA NAHLM AQI-NH₂ | SEQ ID NO: 26 |
| FTLSL DVPTN IMNLL FNIAR ARNLK-(ε-linker-anchor) AQAAA NAHLM AQI-NH₂ | SEQ ID NO: 27 |
| FTLSL DVPTN IMNLL FNIAK AKNLR AQAAA NAHLM AQIK-(ε-linker-anchor)-NH₂ | SEQ ID NO: 28 |
| FTLSL DVPTN IMNLL FNIAR AKNLR AQAAA NAHLM AQIK-(ε-linker-anchor)-NH₂ | SEQ ID NO: 29 |
| FTLSL DVPTN IMNLL FNIAK ARNLR AQAAA NAHLM AQIK-(ε-linker-anchor)-NH₂ | SEQ ID NO: 30 |
| FTLSL DVPTN IMNLL FNIAR ARNLR AQAAA NAHLM AQIK-(ε-linker-anchor)-NH₂ | SEQ ID NO: 31 |

Example 4

Human Stresscopin-Related Peptide (SRP) (43 Amino-acids)

(SEQ ID NO: 78)
HPGSR IVLSL DVPIG LLQIL LEQAR ARAAR EQATT NARIL ARV-NH2

TABLE 4

Modified peptides of human stresseopin-related peptide

| | |
|---|---|
| (anchor-linker) HPGSR IVLSL DVPIG LLQIL LEQAR ARAAR EQATT NARIL ARV-NH2 | SEQ ID NO: 32 |
| HPGSK-(ε-linker-anchor) IVLSL DVPIG LLQIL LEQAR ARAAR EQATT NARIL ARV-NH2 | SEQ ID NO: 33 |
| HPGSR IVLSL DVPIG LLQIL LEQAK-(ε-linker-anchor) ARAAR EQATT NARIL ARV-NH2 | SEQ ID NO: 34 |
| HPGSR WLSL DVPIG LLQIL LEQAR AK-(ε-linker-anchor) AAR EQATT NARIL ARV-NH2 | SEQ ID NO: 35 |
| HPGSR IVLSL DVPIG LLQIL LEQAR ARAAK-(ε-linker-anchor) EQATT NARIL ARV-NH2 | SEQ ID NO: 36 |

TABLE 4-continued

Modified peptides of human stresseopin-related peptide

| | |
|---|---|
| HPGSR IVLSL DVPIG LLQIL LEQAR ARAAR EQATT NAK-(ε-linker-anchor)IL ARV-NH2 | SEQ ID NO: 37 |
| HPGSR IVLSL DVPIG LLQIL LEQAR ARAAR EQATT NARIL AK-(ε-linker-anchor)V-NH2 | SEQ ID NO: 38 |
| HPGSR IVLSL DVPIG LLQIL LEQAR ARAAR EQATT NARIL ARVK-(ε-linker-anchor)-NH2 | SEQ ID NO: 39 |

Example 5

Human Stresscopin (SCP) (40 Amino-acids)

(SEQ ID NO: 79)
TKFTL SLDVP TNIMN LLFNI AKAKN LRAQA AANAH LMAQI-NH2

TABLE 5

Modified peptides of human stresscopin

| | |
|---|---|
| (anchor-linker)TKFTL SLDVP TNIMN LLFNI AKAKN LRAQA AANAH LMAQI-NH2 | SEQ ID NO: 40 |
| (anchor-linker)TRFTL SLDVP TNIMN LLFNI ARARN LRAQA AANAH LMAQI-NH2 | SEQ ID NO: 41 |
| (anchor-linker)TRFTL SLDVP TNIMN LLFNI ARAKN LRAQA AANAH LMAQI-NH2 | SEQ ID NO: 42 |
| (anchor-linker)TRFTL SLDVP TNIMN LLFNI AKARN LRAQA AANAH LMAQI-NH2 | SEQ ID NO: 43 |
| (anchor-linker)TKFTL SLDVP TNIMN LLFNI ARARN LRAQA AANAH LMAQI-NH2 | SEQ ID NO: 44 |
| (anchor-linker)TRFTL SLDVP TNIMN LLFNI AKAKN LRAQA AANAH LMAQI-NH2 | SEQ ID NO: 45 |
| (anchor-linker)TKFTL SLDVP TNIMN LLFNI ARAKN LRAQA AANAH LMAQI-NH2 | SEQ ID NO: 46 |
| (anclior-linker)TKFTL SLDVP TNIMN LLFM AKARN LRAQA AANAH LMAQI-NH2 | SEQ ID NO: 47 |
| TK-(ε-linker-anchor)FTL SLDVP TNIMN LLFNI AKAKN LRAQA AANAH LMAQI-NH2 | SEQ ID NO: 48 |
| TK-(ε-linker-anchor)FTL SLDVP TNIMN LLFNI ARAKN LRAQA AANAH LMAQI-NH2 | SEQ ID NO: 49 |
| TK-(ε-linker-anchor)FTL SLDVP TNIMN LLFNI AKARN LRAQA AANAH LMAQI-NH2 | SEQ ID NO: 50 |
| TK-(ε-linker-anchor)FTL SLDVP TNIMN LLFNI ARARN LRAQA AANAH LMAQI-NH2 | SEQ ID NO: 51 |
| TKFTL SLDVP TNIMN LLFNI AK-(ε-linker-anchor)AKN LRAQA AANAH LMAQI-NH2 | SEQ ID NO: 52 |
| TRFTL SLDVP TNIMN LLFNI AK-(ε-linker-anchor)AKN LRAQA AANAH LMAQI-NH2 | SEQ ID NO: 53 |
| TKFTL SLDVP TNIMN LLFNI AK-(ε-linker-anchor)ARN LRAQA AANAH LMAQI-NH2 | SEQ ID NO: 54 |

TABLE 5-continued

Modified peptides of human stresscopin

| | |
|---|---|
| TRFTL SLDVP TNIMN LLFNI AK-(ε-linker-anchor)ARN LRAQA AANAH LMAQI-NH2 | SEQ ID NO: 55 |
| TKFTL SLDVP TNIMN LLFNI AKAK-(ε-linker-anchor)N LRAQA AANAH LMAQI-NH2 | SEQ ID NO: 56 |
| TRFTL SLDVP TNIMN LLFNI AKAK-(ε-linker-anchor)N LRAQA AANAH LMAQI-NH2 | SEQ ID NO: 57 |
| TKFTL SLDVP TNIMN LLFNI ARAK-(ε-linker-anchor)N LRAQA AANAH LMAQI-NH2 | SEQ ID NO: 58 |
| TRFTL SLDVP TNIMN LLFNI ARAK-(ε-linker-anchor)N LRAQA AANAH LMAQI-NH2 | SEQ ID NO: 59 |
| TKFTL SLDVP TNIMN LLFNI AKAKN LK-(ε-linker-anchor)AQA AANAH LMAQI-NH2 | SEQ ID NO: 60 |
| TRFTL SLDVP TNIMN LLFNI ARARN LK-(ε-linker-anchor)AQA AANAH LMAQI-NH2 | SEQ ID NO: 61 |
| TRFTL SLDVP TNIMN LLFNI ARAKN LK-(ε-linker-anchor)AQA AANAH LMAQI-NH2 | SEQ ID NO: 62 |
| TRFTL SLDVP TNIMN LLFNI AKARN LK-(ε-linker-anchor)AQA AANAH LMAQI-NH2 | SEQ ID NO: 63 |
| TKFTL SLDVP TNIMN LLFNI ARARN LK-(ε-linker-anchor)AQA AANAH LMAQI-NH2 | SEQ ID NO: 64 |
| TRFTL SLDVP TNIMN LLFNI AKAKN LK-(ε-linker-anchor)AQA AANAH LMAQI-NH2 | SEQ ID NO: 65 |
| TKFTL SLDVP TNIMN LLFNI ARAKN LK-(ε-linker-anchor)AQA AANAH LMAQI-NH2 | SEQ ID NO: 66 |
| TKFTL SLDVP TNIMN LLFNI AKARN LK-(ε-linker-anchor)AQA AANAH LMAQI-NH2 | SEQ ID NO: 67 |
| TKFTL SLDVP TNIMN LLFNI AKAKN LRAQA AANAH LMAQI K-(ε-linker-anchor)-NH2 | SEQ ID NO: 68 |
| TRFTL SLDVP TNIMN LLFNI ARARN LRAQA AANAH LMAQI K-(ε-linker-anchor)-NH2 | SEQ ID NO: 69 |
| TRFTL SLDVP TNIMN LLFNI ARAKN LRAQA AANAH LMAQI K-(ε-linker-anchor)-NH2 | SEQ ID NO: 70 |
| TRFTL SLDVP TNIMN LLFNI AKARN LRAQA AANAH LMAQI K-(ε-linker-anchor)-NH2 | SEQ ID NO: 71 |
| TKFTL SLDVP TNIMN LLFNI ARARN LRAQA AANAH LMAQI K-(ε-linker-anchor)-NH2 | SEQ ID NO: 72 |
| TRFTL SLDVP TNIMN LLFNI AKAKN LRAQA AANAH LMAQI K-(ε-linker-anchor)-NH2 | SEQ ID NO: 73 |
| TKFTL SLDVP TNIMN LLFNI ARAKN LRAQA AANAH LMAQI K-(ε-Ilinker-anchor)-NH2 | SEQ ID NO: 74 |
| TKFTL SLDVP TNIMN LLFM AKARN LRAQA AANAH LMAQI K-(ε-linker-anchor)-NH2 | SEQ ID NO: 75 |

Example 6

Modified Peptides and Conjugates

TABLE 6

Modified peptides and Conjugates

| | |
|---|---|
| DNPSL SIDLT FHLLR TLLEL AK-(ε-AEEA-MPA)TQS QRERA EQNRI IFDSV-NH2 (Ucn1) | SEQ ID NO: 80 |
| (MPA-AEEA)IVLSL DVPIG LLQIL LEQAR ARAAR EQATT NARIL ARV-NH2 (Ucn2) | SEQ ID NO: 81 |
| TVLSL DVPIG LLQIL LEQAK-(ε-AEEA-MPA) ARAAR EQATT NARIL ARV-NH2 (Ucn2) | SEQ ID NO: 82 |
| IVLSL DVPIG LLQIL LEQAR AK-(ε-AEEA-MPA)AAR EQATT NARIL ARV-NH2 (Ucn2) | SEQ ID NO: 83 |
| IVLSL DVPIG LLQIL LEQAR ARAAK-(ε-AEEA-MPA) EQATT NARIL ARV-NH2 (Ucn2) | SEQ ID NO: 84 |
| FTLSL DVPTN IMNLL FNIAK(ε-AEEA-MPA) ARNLR AQAAA NAHLM AQI-NH2 (Ucn3) | SEQ ID NO: 85 |
| DNPSL SIDLT FHLLR TLLEL AK-(ε-AEEA-MPA residue-albumin)TQS QRERA EQNRI IFDSV-NH2 (Ucn1) | SEQ ID NO: 86 |
| (albumin-MPA residue-AEEA)IVLSL DVPIG LLQIL LEQAR ARAAR EQATT NARIL ARV-NH2 (Ucn2) | SEQ ID NO: 87 |
| IVLSL DVPIG LLQIL LEQAK-(ε-AEEA- MPA residue-albumin) ARAAR EQATT NARIL ARV-NH2 (Ucn2) | SEQ ID NO: 88 |
| IVLSL DVPIG LLQIL LEQAR AK-(ε-AEEA-MPA residue-albumin)AAR EQATT NARIL ARV-NH2 (Ucn2) | SEQ ID NO: 89 |
| IVLSL DVPIG LLQIL LEQAR ARAAK-(ε-AEEA- MPA residue-albumin) EQATT NARIL ARV-NH2 (Ucn2) | SEQ ID NO: 90 |
| FTLSL DVPTN IMNLL FNIAK(ε-AEEA-MPA residue-albumin) ARNLR AQAAA NAHLM AQI-NH2 (Ucn3) | SEQ ID NO: 91 |

In the above table, "residue" designates the residue of the reaction of MPA with the free thiol of an albumin during the generation of a conjugate as described in Section II.

Example 7

In Vivo Analysis of Biological Activity

The potency of several modified urocortin derivatives were determined by measuring food intake in mice. A study was performed with native human urocortin 1, 2 and 3 to select a dose and to determine whether the IV route was adequate for native peptides. Following the initial study, two additional studies were performed in which the effect of modified derivatives and native peptides were compared.

Tested Sequences:
Human Urocortin 1

(SEQ ID No: 1)
DNPSL SIDLT FHLLR TLLEL ARTQS QRERA EQNRI IFDSV-NH2

Modified Peptide of Human Urocortin 1

(SEQ ID No. 80)
DNPSL SIDLT FHLLR TLLEL AK-(ε ε-AEEA-MPA)TQS QRERA EQNRI IFDSV-NH₂

Human Urocortin 2

(SEQ ID No. 76)
IVLSL DVPIG LLQIL LEQAR ARAAR EQATT NARIL ARV-NH₂

(SEQ ID No. 92)
IVLSL DVPIG LLQIL LEQAR ARAAR EQATT NARIL ARVGH C-NH₂

Modified Peptides of Human Urocortin 2

(SEQ ID No. 81)
(MPA-AEEA) IVLSL DVPIG LLQIL LEQAR ARAAR EQATT NARIL ARV-NH₂

(SEQ ID No. 82)
IVLSL DVPIG LLQIL LEQAK-(ε-AEEA-MPA) ARAAR EQATT NARIL ARV-NH₂

(SEQ ID No. 83)
IVLSL DVPIG LLQIL LEQAR AK-(ε-AEEA-MPA) AAR EQATT NARIL ARV-NH₂

(SEQ ID No. 84)
IVLSL DVPIG LLQIL LEQAR ARAAK-(ε-AEEA-MPA) EQATT NARIL ARV-NH₂

Human Urocortin 3

(SEQ ID No. 77)
FTLSL DVPTN IMNLL FNIAK AKNLR AQAAA NAHLM AQI-NH₂

Modified Peptide of Human Urocortin 3

(SEQ ID No. 85)
FTLSL DVPTN IMNLL FNIAK(ε-AEEA-MPA) ARNLR AQAAA NAHLM AQI-NH₂

Protocol:

Male C57BL/6 mice (22-26g) were housed 3 per cage and fed with standard chow. The night before dosing, mice were food restricted i.e., they were given only half of the amount of food ingested during the previous night. Dosing was performed between 9 and 10 a.m. Mice received a single intravenous injection (5 ml/kg via the tail vein) of saline or urocortin derivatives diluted in saline. Food intake was measured by placing preweighed pellets in the cage and weighing the uneaten pellets at 1, 2, 4, 6, 24 and 48 hours postdose.

Study No. 1 Results:

As shown in FIG. 1, human urocortin 2 injected IV (SEQ ID No. 92) potently reduced food intake up to 1 hour postdose, then food intake was back to the control in the 1-2 h hour time period. Modified urocortin derivatives (SEQ ID No. 81, 82, 83 and 84) inhibited food intake over a 4 to 6 hour-time period. In the 4-6 hour time interval, SEQ ID No. 83 still inhibited food intake by 50% as compared to the control group.

Figure 2:
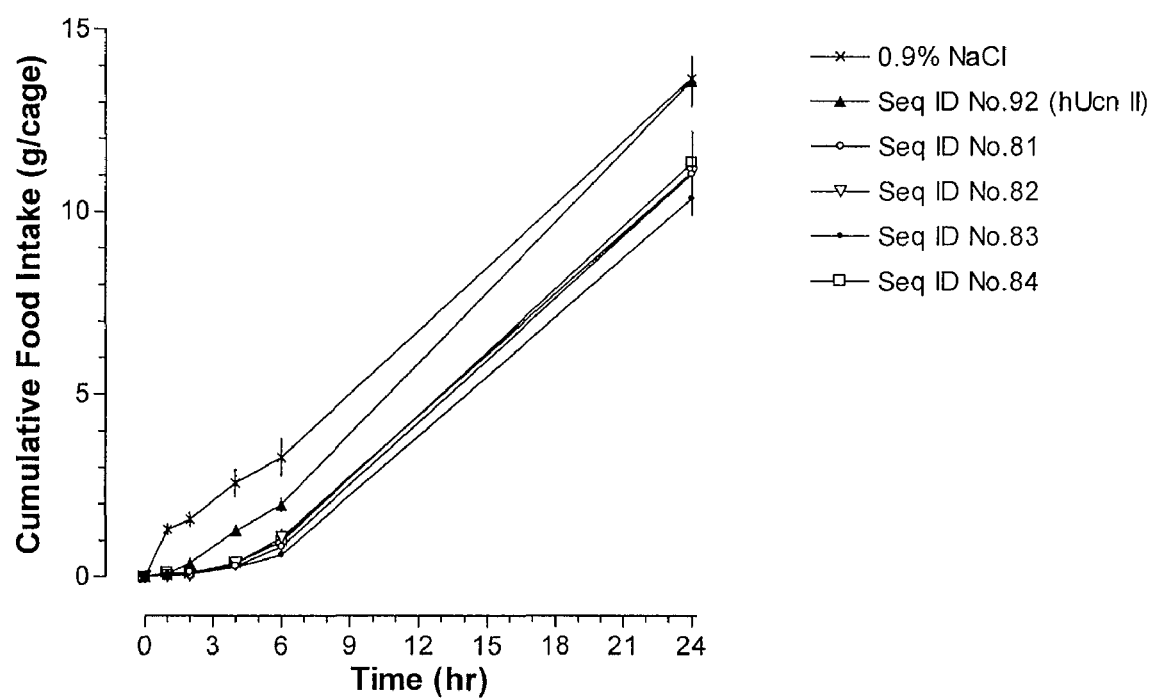
FIG. 2 is a graph depicting the effect of human urocortin 2 derivatives on cumulative food intake in normal mice. Compounds were injected intravenously at 85 nmol/kg. Results are expressed as mean ±SE of 4 cages per group (n=3 mice/cage).

Alternatively, the cumulative food intake (FIG. 2) can be measured. In that case, the effect of human urocortin 2 is still lower than the saline control at 6 hours postdose while modified peptides effects were prolonged up to 24 hours postdose.

Figure 3:
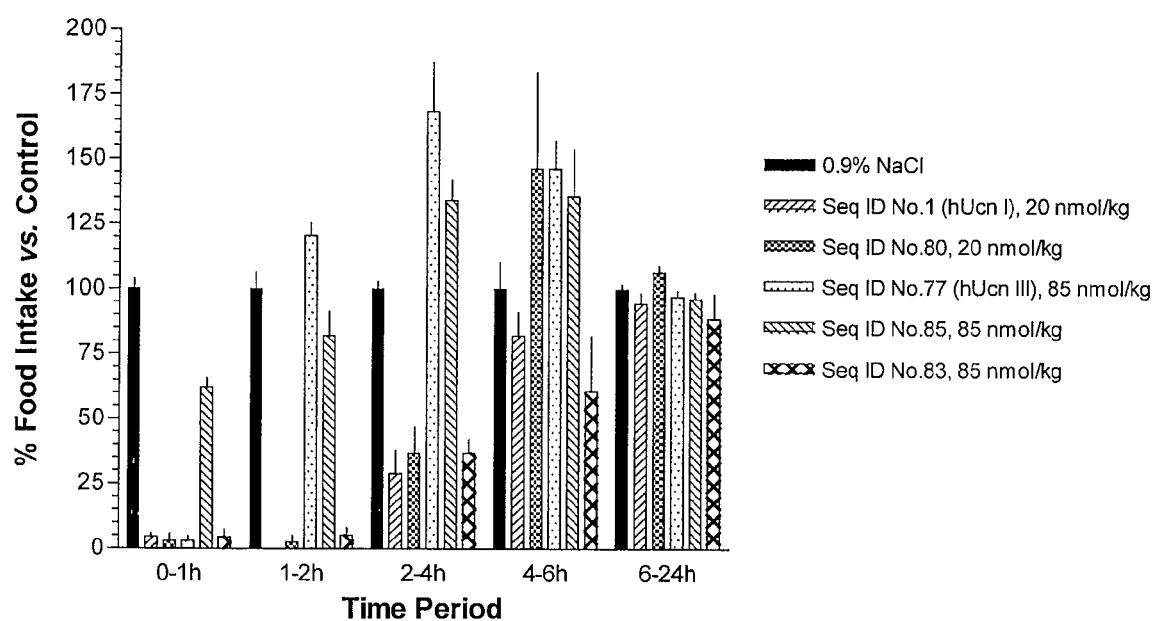
FIG. 3 is a graph depicting the effect of human urocortin derivatives on food intake in normal mice. Compounds were injected intravenously at 20 nmol/kg for urocortin 1 derivatives (Ucn I derivatives) or 85 mmol/kg for urocortin 2 and urocortin 3 derivatives (Ucn II and III derivatives). Results are expressed as mean ±SE of 4 cages per group (n=3 mice/cage).
Figure 4:
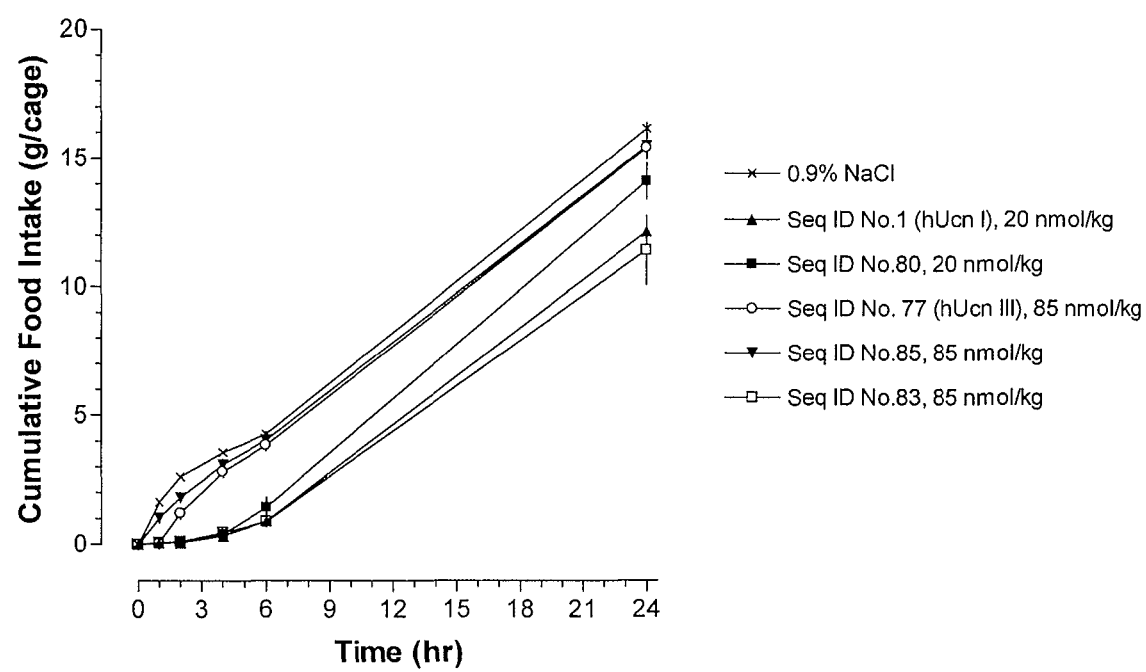
FIG. 4 is a graph depicting the effect of human urocortin derivatives on cumulative food intake in normal mice. Compounds were injected intravenously at 20 nmol/kg for Ucn I derivatives or 85 nmol/kg for Ucn II and III derivatives. Results are expressed as mean ±SE of 4 cages per group (n=3 mice/cage).

Study No. 2 Results:

As shown in FIG. 3, human urocortin 1 potently reduced food intake up to 4 hours following intravenous administration. The corresponding modified Ucn I (SEQ ID No. 80) had similar activity but did not show any prolonged effect versus the free peptide. Urocortin III decreased food intake during the first hour after injection only and the corresponding modified Ucn III (SEQ ID No. 77) was much less active than the free peptide. A 'rebound', i.e., increase of food intake as compared to the control, was observed with the compounds of SEQ ID No: 80, 77 and 85. The modified Ucn II (SEQ ID No. 83) displayed the most prolonged activity.

All references cited herein are incorporated herein by reference in their entirety and for all purposes to the same extent as if each individual publication or patent or patent application was specifically and individually indicated to be incorporated by reference in its entirety for all purposes.

A number of embodiments of the invention have been described. Nevertheless, it will be understood that various modifications may be made without departing from the spirit and scope of the invention. Accordingly, other embodiments are within the scope of the following claims.

---

What is claimed is:

1. A conjugate comprising a modified urocortin-2 peptide derivative, wherein the urocortin-2 peptide derivative comprises the amino acid sequence of SEQ ID NO: 76 with one amino acid substitution, wherein the amino acid at position 20, 22, or 25 of SEQ ID NO: 76 is substituted to lysine,
   wherein the urocortin-2 peptide derivative is modified by the covalent attachment of a reactive group to the urocortin-2 peptide derivative through a linking group, wherein the covalent attachment is at the epsilon amino group of the lysine in the urocortin-2 peptide derivative, wherein the reactive group is maleimido propionic acid (MPA), wherein the linking group is [2-(2-amino) ethoxy)]lethoxy acetic acid (AEEA), and
   wherein the reactive group is covalently attached to an albumin.

2. The conjugate of claim 1, wherein the reactive group is covalently attached to the albumin through the thiol group of cysteine 34 of the albumin.

3. The conjugate of claim 1 or 2, wherein the albumin is recombinant albumin.

4. The conjugate of claim 1 or 2, wherein the albumin is human albumin.

5. A pharmaceutical composition comprising the conjugate of claim 1 or 2, and a pharmaceutically acceptable carrier, excipient, or diluent.

6. A kit comprising in one or more containers the conjugate of claim 1 or 2.

7. The kit of claim 6, wherein the conjugate is in lyophilized form.

8. The kit of claim 7, further comprising a container of sterile solution suitable for reconstituting the lyophilized conjugate.

9. The kit of claim 6, wherein the conjugate is in liquid form.

10. A syringe containing in a solution the conjugate of claim 1 or 2.

11. The conjugate of claim 1 or 2, wherein the urocortin-2 peptide derivative comprises the amino acid sequence of SEQ ID NO: 76 with one amino acid substitution, wherein the amino acid at position 20 of SEQ ID NO: 76 substituted to lysine.

12. The conjugate of claim 1 or 2, wherein the urocortin-2 peptide derivative comprises the amino acid sequence of SEQ ID NO: 76 with one amino acid substitution, wherein the amino acid at position 22 of SEQ ID NO: 76 is substituted to lysine.

13. The conjugate of claim 1 or 2, wherein the urocortin-2 peptide derivative comprises the amino acid sequence of SEQ ID NO: 76 with one amino acid substitution, wherein the amino acid at position 25 of SEQ ID NO: 76 is substituted to lysine.

14. The conjugate of claim 1 or 2, wherein the albumin is purified from blood.

* * * * *